(12) United States Patent
Yodfat et al.

(10) Patent No.: US 8,773,257 B2
(45) Date of Patent: Jul. 8, 2014

(54) SKIN-PATCH TYPE INFUSION PUMP COMPRISING A RESONANT BUZZER

(75) Inventors: Ofer Yodfat, Modi'in (IL); Shai Ben-David, Ramat Ishai (IL); Danna Perlman, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 624 days.

(21) Appl. No.: 13/062,582

(22) PCT Filed: Sep. 3, 2009

(86) PCT No.: PCT/IL2009/000852
§ 371 (c)(1),
(2), (4) Date: May 25, 2011

(87) PCT Pub. No.: WO2010/026580
PCT Pub. Date: Mar. 11, 2010

(65) Prior Publication Data
US 2011/0221583 A1    Sep. 15, 2011

Related U.S. Application Data

(60) Provisional application No. 61/094,522, filed on Sep. 5, 2008.

(51) Int. Cl.
*G08B 1/08* (2006.01)
(52) U.S. Cl.
USPC ............. 340/539.12; 340/539.11; 340/388.4; 340/388.1; 340/387.1; 340/384.6; 340/391.1; 381/396; 381/345
(58) Field of Classification Search
USPC .......... 340/388.4, 388.1, 791.1, 387.1, 384.6, 340/384.1, 539.11, 539.12, 391.1; 381/396, 381/345
See application file for complete search history.

(56) References Cited

U.S. PATENT DOCUMENTS

| 3,631,847 A | 1/1972 | Hobbs, II |
| 3,771,694 A | 11/1973 | Kaminski |

(Continued)

FOREIGN PATENT DOCUMENTS

| WO | WO 2007/052277 | 5/2007 |
| WO | WO 2008/012817 | 1/2008 |

(Continued)

OTHER PUBLICATIONS

International Search Report for PCT Application No. PCT/IL2009/000852.

(Continued)

*Primary Examiner* — Andrew Bee
(74) *Attorney, Agent, or Firm* — Roche Diagnostics Operations, Inc.

(57) ABSTRACT

Disclosed are methods and devices that include a therapeutic fluid dispensing device (10) to deliver a therapeutic fluid into a body of a patient. The device includes a controller to control one or more of fluid delivery operations and notification operations, at least one auditory notifier (800) to produce one or more acoustic signals in response to application of one or more activation signals by the controller and a plurality of electrical contacts coupled to the at least one auditory notifier to enable the application of the one or more activation signals to the at least one auditory notifier. The device also includes at least one housing retaining the at least one auditory notifier therein, the at least one housing being structured to resonate at least one of the one or more acoustic signals produced by the at least one auditory notifier in response to application of at least one of the one or more activation signals.

23 Claims, 16 Drawing Sheets

(56) References Cited

U.S. PATENT DOCUMENTS

| | | | |
|---|---|---|---|
| 4,275,388 A | 6/1981 | Hornung | |
| 4,498,843 A | 2/1985 | Schneider et al. | |
| 4,544,369 A | 10/1985 | Skakoon et al. | |
| 4,657,486 A | 4/1987 | Stempfle et al. | |
| 5,414,406 A * | 5/1995 | Baxter | 340/388.1 |
| 5,957,895 A | 9/1999 | Sage et al. | |
| 6,485,461 B1 | 11/2002 | Mason et al. | |
| 6,589,229 B1 | 7/2003 | Connelly et al. | |
| 6,723,072 B2 | 4/2004 | Flaherty et al. | |
| 6,740,059 B2 | 5/2004 | Flaherty | |
| 2007/0106218 A1 | 5/2007 | Yodfat et al. | |
| 2007/0191702 A1 | 8/2007 | Yodfat et al. | |
| 2008/0125700 A1 | 5/2008 | Moberg et al. | |
| 2008/0215035 A1 | 9/2008 | Yodfat et al. | |
| 2010/0217230 A1 | 8/2010 | Yodfat et al. | |

FOREIGN PATENT DOCUMENTS

| | | |
|---|---|---|
| WO | WO 2008/077914 | 7/2008 |
| WO | WO 2008/078318 | 7/2008 |
| WO | WO 2009/013734 | 1/2009 |
| WO | WO 2009/013735 | 1/2009 |
| WO | WO 2009/013736 | 1/2009 |
| WO | WO 2009/016636 | 2/2009 |
| WO | WO 2009/125398 | 10/2009 |

OTHER PUBLICATIONS

Written Opinion of International Search Authority for PCT Application No. PCT/IL2009/000852.

* cited by examiner

SKIN-PATCH TYPE INFUSION PUMP COMPRISING A RESONANT BUZZER

CROSS-REFERENCE TO RELATED APPLICATIONS

The present application is a 35 U.S.C. 371 national stage entry of PCT/IL2009/000852, which has an international filing date of Sep. 3, 2009 and claims priority to provisional U.S. application Ser. No. 61/094,522, entitled "Auditory Notification Device," filed Sep. 5, 2008, the content of which is hereby incorporated by reference in its entirety.

FIELD

The present disclosure relates generally to a method and a device for sustained infusion of fluids. More particularly, the present disclosure relates to a portable infusion device comprising at least two parts. Even more particularly, the present disclosure relates to a skin securable dispensing unit comprising a reusable part and a disposable part. In some embodiments, a two-part dispensing unit is provided which includes an auditory notification component (notifier). In addition, some embodiments include a system and a method for self-calibration of such an auditory notification component.

BACKGROUND

Medical treatment of several illnesses requires continuous drug infusion into various body compartments, such as subcutaneous and intra-venous injections. Diabetes mellitus (DM) patients, for example, require the administration of varying amounts of insulin throughout the day to control their blood glucose levels. In recent years, ambulatory portable insulin infusion pumps have emerged as an alternative to multiple daily syringe injections of insulin, initially for Type 1 diabetes patients and subsequently for Type 2 diabetes patients. These pumps, which deliver insulin at a continuous (or periodic) basal rate, as well as in bolus volumes, were developed to liberate patients from repeated self-administered injections, and to allow them to maintain a normal or near-normal daily routine. Both basal and bolus volumes are generally delivered in precise doses, according to individual prescription, because an overdose or under-dose of insulin could be fatal.

The first generation of portable insulin pumps includes "pager like" devices with a reservoir contained within a housing. A long tube is provided for delivering insulin from the pump attached to a patient's belt to a remote insertion site. Examples of such devices are disclosed, for example, in U.S. Pat. Nos. 3,631,847, 3,771,694, 4,657,486 and 4,544,369, the contents of all of which are hereby incorporated by reference in their entireties. These devices represent an improvement over the requirement of multiple daily injections, but have drawbacks, among which are the large size and weight of the devices, the long tubing which limits the daily activities of the devices' users, and lack of discreetness.

To avoid the limitations associated with first generation infusion pumps, a new concept was proposed, which was implemented in second generation pumps. The new concept is predicated on the use of a remote contained skin-adherable device with a housing having a bottom surface adapted to be in contact with the patient's skin, a reservoir disposed within the housing, and an injection needle in fluid communication with the reservoir. These skin adherable devices are configured to generally be replaced every 2-3 days, similarly to currently available pump infusion sets. This paradigm is described, for example, in U.S. Pat. Nos. 4,498,843, 5,957,895, 6,589,229, 6,740,059, 6,723,072 and 6,485,461, the contents of all of which are hereby incorporated by reference in their entireties. These second generation skin securable devices also have several drawbacks. For example the entire device has to be typically disposed-of every 2-3 days, resulting in the devices' expensive components (such as electronics, driving mechanism, etc.) also being disposed of.

Third generation skin-adherable devices were developed to avoid the cost issues associated with second generation devices and to extend patient customization. An example of such a device was described in co-owned/co-pending. U.S. Patent publication no. 2007-0106218 and International Patent publication no. WO/2007/052277, the contents of all of which are hereby incorporated by reference in their entireties. Such a third generation device contains a remote control unit and a skin-adherable patch unit (also referred to as "dispensing patch unit" or "dispensing unit") that may include two parts: (1) a reusable part containing the electronics, at least a portion of the driving mechanism and other relatively expensive components, and (2) a disposable part containing the reservoir and, in some embodiments, at least one power source (e.g., a battery). A tube can also be provided which delivers the fluid from the reservoir to an outlet port that contains a connecting lumen.

This concept can provide a cost-effective skin-adherable infusion device and enables device versatility in terms of the various reservoir sizes that may be used, the various needle and cannula types that may be used, etc.

A skin-adherable fluid (e.g., insulin) delivery device was also disclosed in co-owned, co-pending U.S. patent application Ser. No. 11/989,681 and International Patent publication no. WO/2008/012817, both filed Jul. 24, 2007 and both claiming priority to U.S. Provisional Patent Applications Nos. 60/833,110, filed Jul. 24, 2006, and 60/837,877, filed Aug. 14, 2006, both entitled "Systems, Devices, and Methods for Fluid/Drug Delivery", the contents of all of which are hereby incorporated by reference in their entireties.

A fourth generation infusion device is disclosed in co-owned, co-pending U.S. Patent publication no. 2008-0215035 and International Patent publication no. WO/2008/078318, both filed Dec. 20, 2007, claiming priority to U.S. Provisional Patent Application No. 60/876,679, filed Dec. 22, 2006, entitled "Systems, Devices, and Methods for Sustained Delivery of a Therapeutic Fluid", the contents of all of which are hereby incorporated by reference in their entireties.

Fourth generation devices are configured as dispensing units that can be disconnected and reconnected to a skin-adherable cradle unit. Fourth generation skin-securable dispensing units can be remotely controlled and/or can be operated by a user interface (e.g., a buttons-based interface) that are located on the dispensing unit's housing (and/or, in some embodiments, on the reusable part) as disclosed, for example, in the co-owned, co-pending International Patent publication no. WO/2009/013736, filed Jul. 20, 2008, claiming priority to U.S. Provisional Patent Application No. 60/961,527, and entitled "Manually Operable Portable Infusion Pump", and International Patent publication no. WO/2009/016636, filed Jul. 31, 2008, claiming priority to U.S. Provisional Application Ser. Nos. 60/963,148 and 61/004,019, and entitled "Portable infusion device with means for monitoring and controlling fluid delivery", the contents of all of which are hereby incorporated by reference in their entireties.

Co-owned/co-pending U.S. Patent publication no. 2007-0191702, the content of which is hereby incorporated by reference in its entirety, discloses a device that includes a dispensing patch unit (e.g., an insulin dispensing patch) and an analyte sensor (e.g., a continuous glucose monitor). This type of dual function device has a similar configuration to that outlined above and can also be disconnected and reconnected from and to the skin at patient's discretion.

In some embodiments, fluid delivery devices include a notification component (also referred to as a notifier or indicator) for notification purposes, e.g., to notify the user that fluid delivery has started, and/or for alerting purposes, e.g., to alert the user in case of mechanical malfunction or of low battery status. Such a notification component can be located in a skin-securable dispensing unit and/or in a remote control. The notification component can provide auditory output (e.g., a buzzer), visual output (e.g., the notification component can include a display, flashing lights, etc.) or provide tactile output (e.g., a vibrator). An auditory notification component (also referred to as "Buzzer") can employ, for example, a piezoelectric element or a magnetic element, which is typically disposed within a resonance chamber (i.e., a cavity defined by interior surfaces that reflect acoustic/sound waves) in order to amplify the sound generated by the element.

A number of different forms of buzzers, employing piezoelectric elements or transducers to generate a relatively piercing and noticeable audible tone when energized with relatively little power, have come into use. Such systems are activated at or near the resonant frequency of the vibrating piezoelectric element to achieve the most efficient use of available electrical energy and greatest audible output.

In a device for delivering a therapeutic fluid (e.g., insulin) to the body of a patient, it is generally important to maximally amplify the sound generated by the buzzer, since the consequence of not hearing the generated sound can be hazardous, for example, in case of an alert generated upon occlusion detection. The generated sound can be maximally amplified by placing the buzzer inside a suitable resonance chamber and activating it at or near the resonant frequency of the piezoelectric element, i.e., the frequency at which the amplitude of the piezoelectric element's oscillation is the greatest.

However, individual piezoelectric elements often vary in precise resonant frequency, and thus, a manufacturer's data sheet typically specifies only a frequency range within which the actual resonant frequency of the piezoelectric element is guaranteed to lie (e.g. 4.0±0.5 KHz). In addition, placing the piezoelectric element inside a resonance chamber may further affect the resonant frequency of the individual piezoelectric element and contribute to the variation in precise resonant frequency, for example, due to different methods of supporting the element within the chamber (e.g., edge support, node support, etc.). Furthermore, the resonant frequency of a single piezoelectric element itself may vary due to such factors as aging, varying temperature and humidity conditions, etc.

In view of this, self-calibrating systems for determining the actual resonant frequency of an individual piezoelectric element/transducer and for driving/activating the element/transducer at its actual resonant frequency have been proposed. Such a system was described, for example, in U.S. Pat. No. 4,275,388, the content of which is hereby incorporated by reference in its entirety. The system described in that patent, as well as other known self-calibrating systems, is generally implemented using a feedback mechanism (e.g., a feedback electrode). In some embodiments, the feedback mechanism is connected to the piezoelectric element that generates a feedback signal representative of the amount of flexing of the element when driven at different frequencies. The optimum driving frequency is then determined based on the feedback signal.

Despite the hazardous consequences of inefficient buzzers, existing fluid delivery devices generally do not employ such self-calibrating systems. Furthermore, the existing self-calibration systems, which require the use of feedback mechanisms, are not suitable for skin-securable miniature fluid delivery devices due to some of the following reasons:

The need for additional components/modules (e.g., a feedback electrode, contacts) requires enlargement of the device and creates undesirable limitations regarding the spatial arrangement of the buzzer, and other components, within the delivery device.

The piezoelectric buzzer (also referred to as "piezoelectric diaphragm") typically includes a piezoelectric plate (e.g., a ceramic plate, a crystal plate) having electrodes on both sides (together referred to as "piezoelectric element"), and a metal plate (e.g., brass, stainless steel, etc.). Connecting a feedback mechanism to the piezoelectric element reduces the efficiency of the buzzer as it requires a size reduction of one of the element's electrodes.

Implementation of the described self-calibration systems increases the cost (and thus the price to the consumer) of the device as additional components are required.

SUMMARY OF THE DISCLOSURE

Accordingly, in some embodiments, a therapeutic fluid delivery device employing an auditory notification component (which may be hereinafter referred to as a "buzzer") which generates a maximally or optimally amplified sound is provided.

In some embodiments, a therapeutic fluid delivery device employing a buzzer which comprises a piezoelectric element that is activated near or at its resonant frequency is provided.

In some embodiments, a system and a method for self-calibrating a piezoelectric buzzer, which can be employed in a miniature fluid delivery device, are provided.

In some embodiments, a system and a method for self-calibrating a piezoelectric buzzer having low energy consumption behavior, which do not require additional components and are relatively inexpensive, are provided.

In some embodiments, a therapeutic fluid dispensing device to deliver a therapeutic fluid into a body of a patient is provided. The device includes a controller to control one or more of fluid delivery operations and notification operations, at least one auditory notifier to produce one or more acoustic signals in response to application of one or more activation signals by the controller and a plurality of electrical contacts coupled to the at least one auditory notifier to enable the application of the one or more activation signals to the at least one auditory notifier. The device also includes at least one housing retaining the at least one auditory notifier therein, the at least one housing being structured to resonate at least one of the one or more acoustic signals produced by the at least one auditory notifier in response to application of at least one of the one or more activation signals.

Embodiments of the device may include any of the following features.

The at least one auditory notifier may include a piezoelectric element.

The device may further comprise at least one chassis received, at least partly, within the at least one housing.

The at least one auditory notifier may be coupled to the at least one chassis.

One or more of the at least one housing may include a main portion and a cover portion connectable to the main portion, the cover portion may define a first side of a two-sided resonance chamber, and a portion of the at least one chassis may define a second side of the two-sided resonance chamber.

The device may further include a sealing mechanism to maintain sealing of the one or more of the at least one housing upon connection of the cover portion to the main portion.

The at least one chassis may include one or more bores for passage of one or more of the plurality of the electrical contacts therethrough.

The at least one auditory notifier may be disposed within a resonance chamber defined by one or more walls of one or more of: the at least one housing and the at least one chassis. The resonance chamber may be a one-sided resonance chamber. The resonance chamber may be a two-sided resonance chamber.

The at least one housing may include at least one sound emitting aperture. The at least one aperture may be provided with a selective membrane to prevent ingression of fluids into the device. One or more of the at least one sound emitting aperture may be substantially aligned with the at least one auditory notifier.

At least one of the plurality of the electrical contacts may include a spring.

The plurality of the electrical contacts may include two electrical contacts.

The at least one housing may include a reusable part housing including at least part of a reusable part of the device, and a disposable part housing including at least part of a disposable part of the device.

The disposable part may be connectable to the reusable part. The at least one auditory notifier may be retained within the reusable part housing.

At least one of the reusable part housing and the disposable part housing may include one or more sound emitting apertures.

The controller may be further configured to determine at least one resonant frequency of the at least one auditory notifier.

The controller configured to determine the at least one resonant frequency may be configured to apply one or more signals to the at least one auditory notifier, and determine the at least one resonant frequency based on at least one acoustic signal resulting from applying the one or more signals to the at least one auditory notifier.

The one or more applied signals may have pre-determined characteristics including one or more of, for example, a pre-determined amplitude, a pre-determined frequency and/or a pre-determined duration.

The at least one resultant acoustic signal may be substantially sinusoidal, and the controller may further be configured to determine a period of the at least one substantially sinusoidal acoustic signal.

The controller may additionally be configured to determine a corresponding intermediate resonant frequency for each of the at least one acoustic signal resulting from application of each of the one or more signals, and determine the at least one resonant frequency based on the determined intermediate resonant frequency for each of the at least one resulting acoustic signal.

The controller configured to determine the at least one resonant frequency may be configured to apply a plurality of signals to the at least one auditory notifier to generate a corresponding plurality of acoustic signals, each signal in the plurality of applied signals having a corresponding frequency within a frequency range. The controller may further be configured to identify from the corresponding generated plurality of acoustic signals an acoustic signal having the largest amplitude of the respective amplitudes of the generated plurality of acoustic signals, and identify from the plurality of applied signals the applied signal that caused the generation of the acoustic signal having the largest amplitude.

The controller configured to determine the at least one resonant frequency may be configured to apply a plurality of signals to the at least one auditory notifier to generate a corresponding plurality of acoustic signals, each signal in the plurality of applied signals having a corresponding frequency within a frequency range. The controller may further be configured to identify from the corresponding generated plurality of acoustic signals an acoustic signal having the longest duration of the respective durations of the generated plurality of acoustic signals, and identify from the plurality of applied signals the applied signal that caused the generation of the acoustic signal having the longest duration.

The controller configured to determine the at least one resonant frequency may be configured to apply one or more signals to determine the at least one resonant frequency, each of the one or more applied signals having at least one pre-determined characteristic resulting in the generation of respective one or more acoustic signals each having an amplitude lower than a pre-determined audible threshold representative of a minimum amplitude level detectable by a user.

The controller may further be configured to set one or more activation frequencies for the at least one auditory notifier based on the determined resonant frequency.

The one or more activation signals may include a plurality of signal sequences, each of the plurality of signal sequences comprising one or more signals having respective pre-determined characteristics, each of the plurality of signal sequences when applied to the at least one auditory notifier causes a corresponding one of a plurality of acoustic signal sequences to be generated, each of the plurality of acoustic signal sequences comprising one or more acoustic signals and being representative of one or more different operating conditions of the therapeutic fluid dispensing device. The controller may further be configured to select a signal sequence from the plurality of signal sequences and apply the selected signal sequence to the at least one auditory notifier.

The different operating conditions of the therapeutic fluid dispensing device may include one or more of, for example, an alarm condition, a status notification and/or a required operation alert.

In some embodiments, a method to calibrate an auditory notifier disposed within at least one housing of a therapeutic fluid dispensing device is disclosed. The method includes applying one or more signals to the auditory notifier, determining, based on one or more acoustic signals resulting from applying the one or more signals, at least one resonant frequency of the auditory notifier, and setting one or more activation frequencies for the auditory notifier based on the determined at least one resonant frequency.

Embodiments of the method may include one or more of the above described features of the device, as well as any of the following features.

Applying the one or more signals may include applying a single signal to the auditory notifier, and determining the at least one resonant frequency may include determining the at least one resonant frequency based on the acoustic signal resulting from the applied single signal.

The one or more resultant acoustic signals may be substantially sinusoidal, and determining the at least one resonant frequency may include determining a period of the one or more substantially sinusoidal acoustic signals and determining the resonant frequency based on the period of the one or more substantially sinusoidal acoustic signals.

Determining the at least one resonant frequency may include determining for the one or more acoustic signals resulting from application of each of the one or more signals corresponding intermediate resonant frequencies and determining the resonant frequency based on the determined intermediate resonant frequencies.

Determining the resonant frequency based on the determined intermediate resonant frequencies may include determining an average frequency based on the determined intermediate resonant frequencies.

The method may further include storing the determined intermediate resonant frequencies in a memory.

Applying the one or more signals may include applying a plurality of signals to the auditory notifier to generate a corresponding plurality of acoustic signals, each signal in the plurality of applied signals having a corresponding frequency within a frequency range. Determining the at least one resonant frequency may include identifying from the corresponding generated plurality of acoustic signals an acoustic signal having the largest amplitude of the respective amplitudes of the generated plurality of acoustic signals, and identifying from the plurality of applied signals the applied signal that caused the generation of the acoustic signal having the largest amplitude.

Applying the one or more signals may include applying a plurality of signals to the auditory notifier to generate a corresponding plurality of acoustic signals, each signal in the plurality of applied signals having a corresponding frequency within a frequency range. Determining the at least one resonant frequency may include identifying from the corresponding generated plurality of acoustic signals an acoustic signal having the longest duration of the respective durations of the generated plurality of acoustic signals and identifying from the plurality of applied signals the applied signal that caused the generation of the acoustic signal having the longest duration.

Applying the one or more signals may include applying one or more signals, each of the one or more applied signals having at least one pre-determined characteristic resulting in the generation of respective one or more acoustic signals each having an amplitude lower than a pre-determined audible threshold representative of a minimum amplitude level detectable by a user.

Setting the one or more activation frequencies may include setting the at least one determined resonant frequency as one of the one or more activation frequencies.

The method may further include storing the one or more activation frequencies in a memory.

The method may further include repeating the applying, the determining and the setting at pre-determined time instances.

In some embodiments, a method to calibrate an auditory notifier including a piezoelectric element is provided. The method includes sending one or more signals to the piezoelectric element, receiving one or more resultant signals generated by the piezoelectric element in response to the sent one or more signals, determining at least one resonant frequency of the piezoelectric element based on the received one or more resultant signals and setting one or more activation frequencies for activating the piezoelectric element based on the determined at least one resonant frequency of the piezoelectric element.

Embodiments of the above second method may include one or more of the above-described features of the first method and the device.

In some embodiments, a method to calibrate an auditory notifier disposed within at least one housing of a therapeutic fluid dispensing device is provided. The method includes providing a therapeutic fluid dispensing device comprising a reusable part and a disposable part coupleable to the reusable part, applying one or more signals to the auditory notifier upon coupling the disposable part to the reusable part, determining, based on one or more acoustic signals resulting from applying the one or more signals, at least one resonant frequency of the auditory notifier, and setting one or more activation frequencies for the auditory notifier based on the at least one determined resonant frequency.

Embodiments of the above third method may include one or more of the above-described features of the first and second methods and the device.

In some embodiments, a method to generate auditory notifications in a therapeutic fluid dispensing device is provided. The method includes selecting a signal sequence from a plurality of signal sequences, each of the plurality of signal sequences comprising one or more signals having respective pre-determined characteristics, each of the plurality of signal sequences causes, when applied to an auditory notifier disposed within at least one housing of the therapeutic fluid dispensing device, a corresponding one of a plurality of acoustic signal sequences to be generated, each of the generated acoustic signal sequences comprising one or more acoustic signals and being representative of one or more different operating conditions of the therapeutic fluid dispensing device. The method also includes applying the selected signal sequence to the auditory notifier.

Embodiments of the above fourth method may include one or more of the above-described features of the first, second and third methods and the device, as well as any of the following features.

At least one of the plurality of signal sequences may be determined based on at least one determined resonant frequency of the auditory notifier disposed within the at least one housing.

The method may further include determining the at least one resonant frequency, and determining the at least one of the plurality of signal sequences based on the at least one determined resonant frequency.

Details of one or more implementations are set forth in the accompanying drawings and in the description below. Further features, embodiments, aspects, and advantages will become apparent from the description, the drawings, and the claims.

BRIEF DESCRIPTION OF THE DRAWINGS

Some of the embodiments of the present disclosure are described with reference to the accompanying drawings. In the drawings, like reference numbers indicate identical or functionally similar elements.

DETAILED DESCRIPTION

Figure 1:
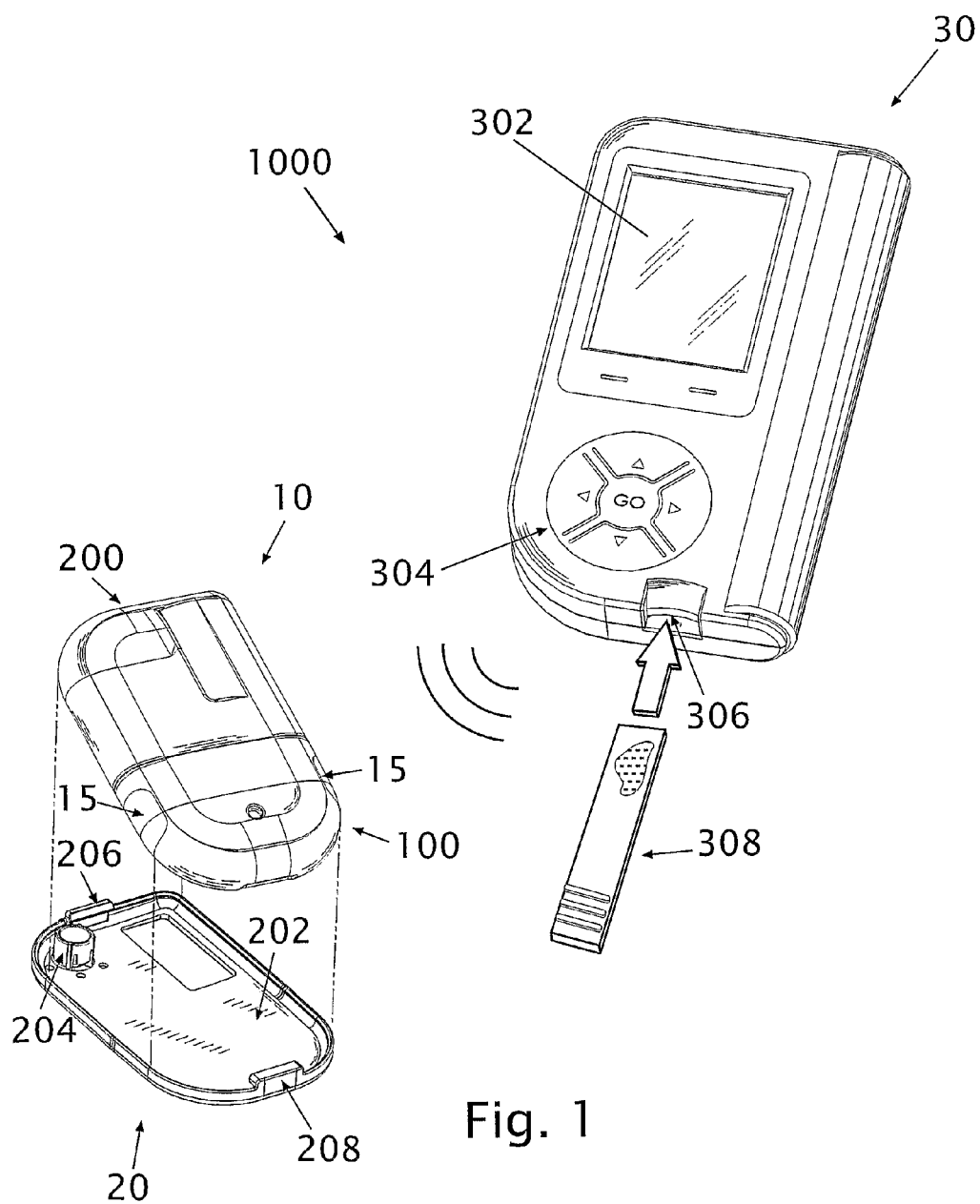
FIG. 1 includes diagrams illustrating a fluid delivery system for medical infusion of therapeutic fluids into a body of a patient according to some embodiments of the disclosure.

Referring to FIG. 1, diagrams illustrating a fluid delivery system 1000 for medical infusion of therapeutic fluid(s) (e.g., insulin) into a body of a patient are shown. In some embodiments, the system 1000 comprises a dispensing unit 10 (or "dispensing device"), a cradle unit 20 and a remote control unit 30. The dispensing unit 10 can be provided with a sensing apparatus for sensing bodily analyte (e.g., glucose). In some embodiments (not shown) the dispensing unit 10 may be attached to the skin directly using an adhesive layer disposed at the bottom surface of the dispensing unit. In some embodiments (not shown) the dispensing unit 10 may be a pager-type device used in conjunction with a skin-adherable infusion set. As used herein, the terms "dispensing unit" and/or "dispensing device" include any medical device that includes a sensor. Additionally, a device may refer to any type of device, e.g., a pager-like device, a skin-adhereable device, etc.

The dispensing unit 10 may be composed of a single part or of two parts. The two-part dispensing unit 10 may include a reusable part 100 and a disposable part 200.

The cradle unit (which may be hereinafter also referred to as a "cradle" or "cradle part") 20 is, in some embodiments, adherable to the patient's skin, and may include a cradle base 202 and a well 204 defining a passageway to enable insertion of a cannula through the cradle unit 20 and into the patient's body. In some embodiments, the well 204 is structured as a protrusion extending radially (e.g., upwardly) from the cradle base 202 to enable alignment and appropriate connection of the dispensing unit 10 to the cradle unit 20. The cradle unit 20 can further include anchoring mechanisms (e.g., latches) 206 and 208 to secure the dispensing unit 10 to the cradle unit 20 after connection and to enable disconnection and reconnection at the patient's discretion. A system employing a cradle unit is described, for example, in co-owned/co-pending U.S. Patent publication no. 2008-0215035 and International Patent publication no. WO/2008/078318.

The remote control unit 30 includes, in some embodiments, a display/screen 302 which can be touch-sensitive and may include a user interface having, for example, operating button(s)/switches 304. It should be noted that the patient/user can also control/instruct/command the operation of the dispensing unit 10 by one or more buttons/switches 15 that may be disposed on the dispensing unit 10. Such buttons/switches 15 are described, for example, in co-pending/co-owned International Patent publication no. WO/2009/013736. Additional operating buttons/switches can be located in the reusable part 100. Additionally, a screen to communicate with the patient/user, as described, for example, in co-pending/co-owned International Patent publication no. WO/2009/016636, may also be provided.

The remote control unit 30 can be used to provide operating instructions, data, etc., to a controller of the dispensing device (e.g., a controller implemented using a processor-based device) of the dispensing unit 10, receive alerts and warnings from the controller, etc., and can be further configured to communicate with the dispensing unit 10 via, for example, wireless communication as well as any other suitable communication technique, for example, by induction, RF transmission, IR transmission etc., or through wired communication.

In some embodiments, the remote control unit 30 may include a blood glucose monitor. Thus, a blood sample can be drawn on a conventional test strip 308 which can be inserted into a dedicated slot 306.

Figure 2A:
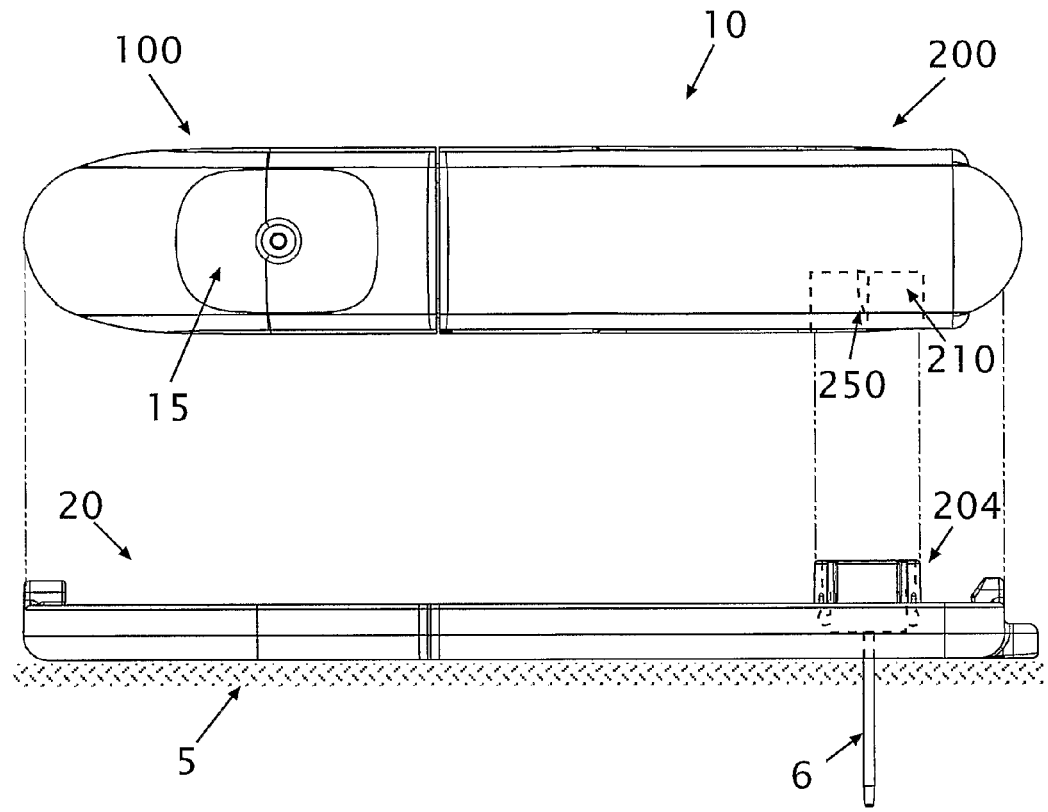
FIGS. 2a-2b are diagrams of a two-part dispensing unit and a cradle unit prior to connection (FIG. 2a) and after connection (FIG. 2b) according to some embodiments of the disclosure.
Figure 2B:
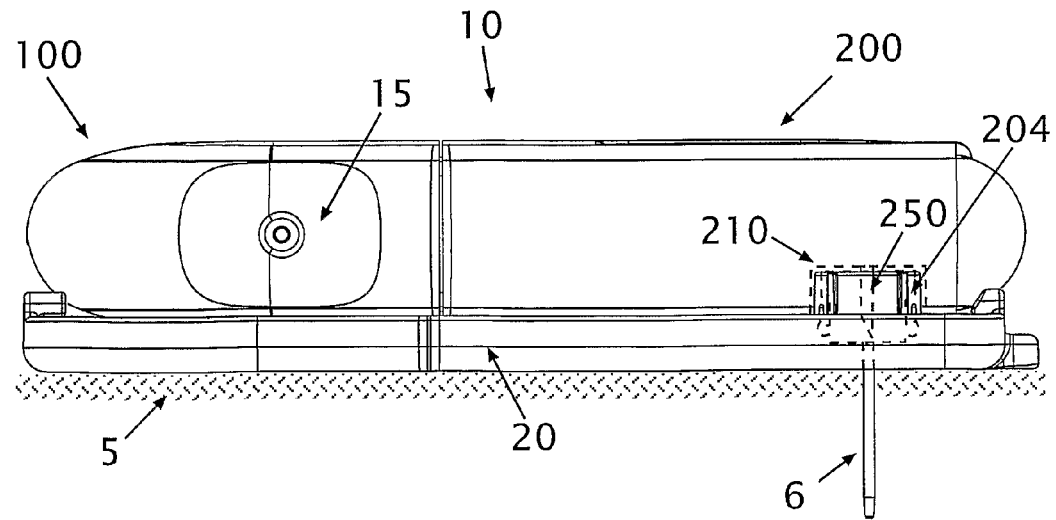

Referring to FIGS. 2a-2b, diagrams of a two-part dispensing unit 10 and a cradle unit 20 prior to connection (FIG. 2a) and after connection (FIG. 2b) are shown. After securing (e.g., adhering) the cradle unit 20 to the skin 5, a cannula 6 is subcutaneously inserted through the cradle unit's well 204. The dispensing unit 10 can then be connected to the cradle unit 20. As shown in the phantom lines in FIG. 2a, the skin-securable dispensing unit 10 includes, on its bottom surface, an outlet port 210 with a connecting lumen 250 configured to be in fluid communication with the patient's/user's body via the cannula 6. In implementations in which the dispensing unit 10 includes two parts, the outlet port 210 and the connecting lumen 250 are located on the bottom surface of the disposable part 200.

Figure 3A:
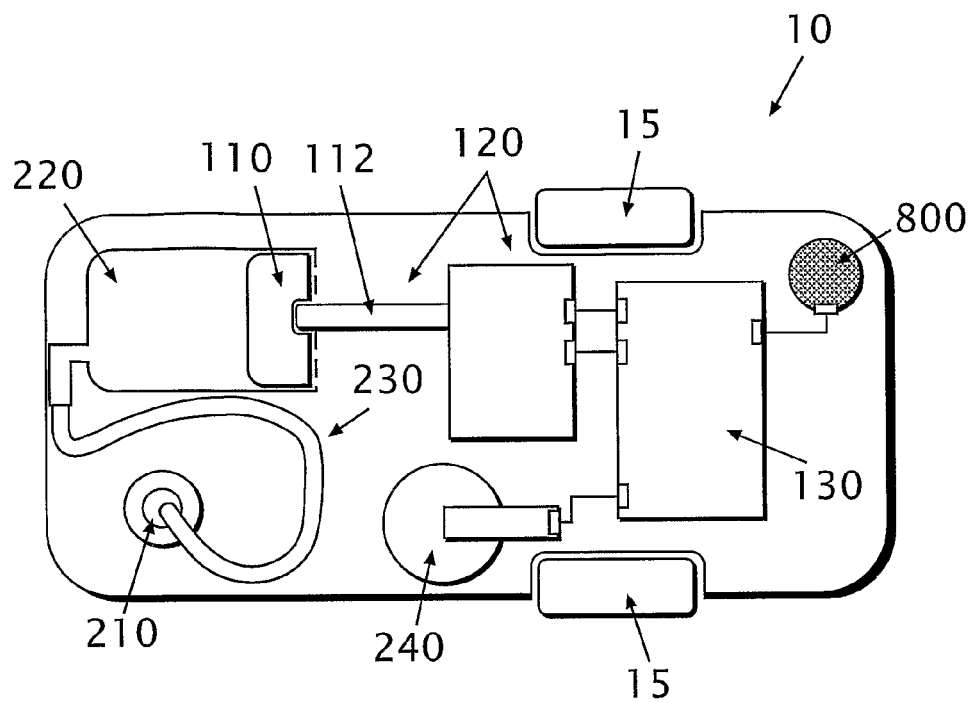
FIGS. 3a-3b are schematic diagrams of a single part dispensing unit (FIG. 3a) and a two-part dispensing unit (FIG. 3b) according to some embodiments of the disclosure.
Figure 3B:
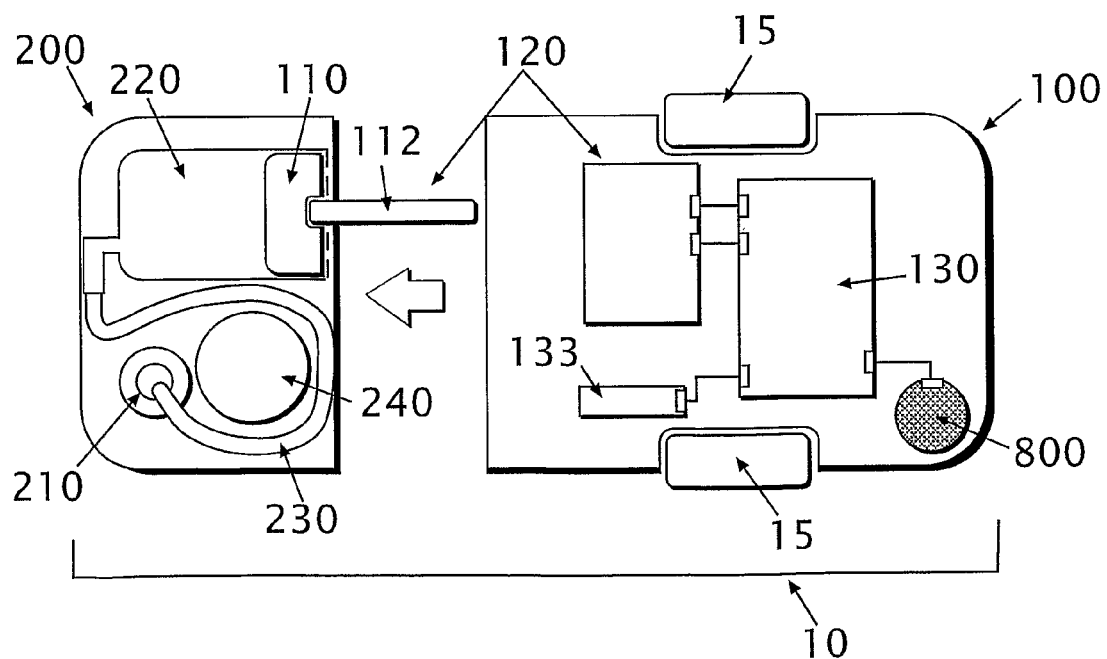

Referring to FIGS. 3a-3b, schematic diagrams of a single part dispensing unit 10 (FIG. 3a) and a two-part dispensing unit (FIG. 3b) are shown. The dispensing units are implemented using, for example, a plunger/piston pumping mechanism for dispensing fluid (e.g., insulin) into the patient's body. In some embodiments, the dispensing unit may include a peristaltic-based pumping mechanism, or any other type of pumping mechanism.

As further shown in FIG. 3a, depicting the single-part dispensing unit 10, the fluid is delivered from a reservoir 220 to the outlet port 210. The reservoir 220 is provided with a piston 110 which, when displaced inside the interior of the reservoir 220, urges the fluid towards the outlet port 210. In some embodiments, the reservoir 220 is fluidly connected to the outlet port 210 via a connecting delivery tube 230. A driving mechanism 120 may be provided, which may include a motor (e.g., a stepper motor, a DC motor, an SMA actuator, or the like) and gears for driving the piston 110. The driving mechanism may further include a piston rod 112 which is mechanically coupled to the piston 110. The driving mechanism 120 may be controlled by electronic components/modules, including a controller/processor (e.g., a CPU, an MCU, etc.) and a transceiver (e.g., for receiving operation instructions from a remote control such as the remote control unit 30 of FIG. 1). The electronic components/modules are denoted in FIG. 3a as reference numeral 130. A suitable power supply/source 240 is also included in the dispensing unit 10. The power source 240 may include one or more batteries, and may also include, or be used in conjunction with, a charge storage device, such as a capacitor. In some embodiments, the power source 240 can be a rechargeable power source (e.g., a rechargeable battery). Infusion programming and control may be performed by a remote control, such as the remote control 30 depicted in FIG. 1 and/or by a user interface that includes one or more buttons 15 provided at the dispensing unit 10.

In some embodiments, the dispensing unit 10 further includes at least one notification component (notifier) 800. The notifier 800 may be an auditory-based notifier (e.g., a buzzer), a visually-based notifier (e.g., a display, flashing lights) or a tactile-based notifier (e.g., a vibrator). An auditory-based notifier can employ, for example, a piezoelectric element or a magnetic element.

As shown in FIG. 3b, the two-part dispensing unit 10 (depicted with the two parts disconnected) includes a reusable part 100 and a disposable part 200 employing, for example, a plunger/piston pumping mechanism. The reusable part 100 may comprise at least a portion of the driving mechanism 120 (e.g., motor and gears), electronic components, designated as reference numeral 130, arranged to implement a controller to control operations of the dispensing unit 10, a user interface including, for example, one or more buttons 15, a notifier 800, and may further comprise other relatively expensive components such as sensors. The disposable part 200 may comprise relatively inexpensive components, including, for example, a reservoir 220 provided with a piston 110 which is coupled to a piston rod 112, a power supply/source 240 (e.g., a battery, which may include a rechargeable and/or a non-rechargeable battery), an outlet port 210, a connecting lumen 250 (shown, for example, in FIGS. 2a-2b) and a connecting delivery tube 230. In some embodiments, the piston rod 112 may be located in the reusable part 100 or it may be shared by both parts of the dispensing unit 10. Similarly, the energy supply 240 may be located in the reusable part 100 or it may be shared by both parts. For example, the disposable part 200 may include a battery and the reusable part may include a capacitor. In some embodiments, the reusable part 100 may comprise electrical contacts 133 (only one electrical contact is shown in FIG. 3b) for establishing electrical connection between the energy source 240 in the disposable part 200 and the electronic components 130 in the reusable part 100 upon connection of the reusable and disposable parts. According to some embodiments, the notifier 800 may be located in the disposable part 200 of the dispensing unit 10.

Infusion programming can be performed by a remote control unit 30 (shown, for example, in FIG. 1) and/or by one or more buttons 15 provided on the reusable part 100. The two-part dispensing unit 10 is operable upon connection of the two parts (100 and 200), as indicated by the single-headed arrow in FIG. 3b.

Figure 4:
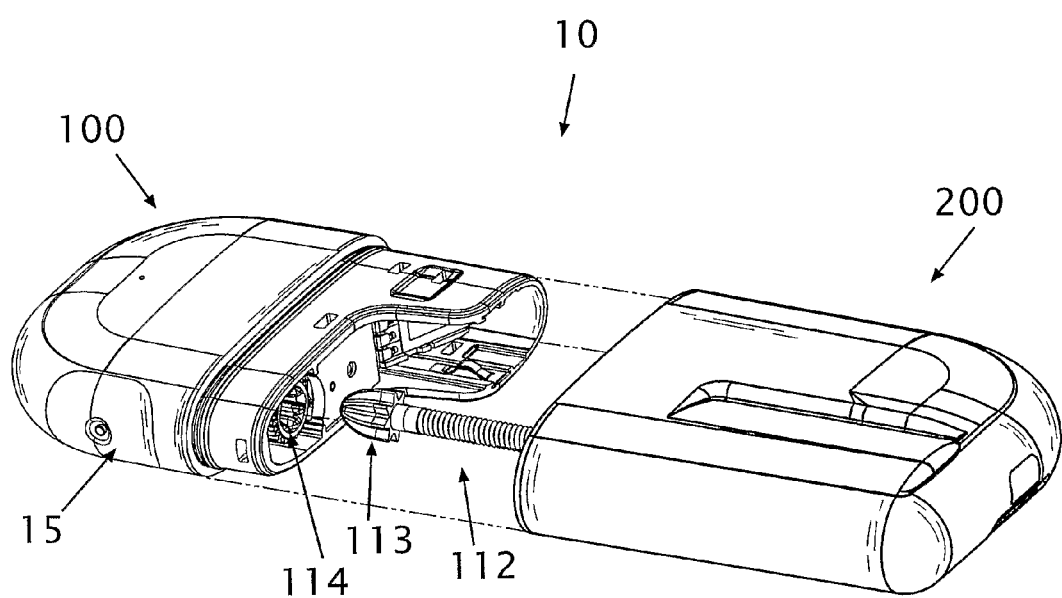
FIG. 4 is a perspective view of a two-part dispensing unit employing a plunger/piston pumping mechanism for dispensing fluid into a patient's body according to some embodiments of the disclosure.

Referring to FIG. 4, a perspective view of a two-part dispensing unit 10 employing a plunger/piston pumping mechanism for dispensing fluid into a patient's body is shown. In the shown embodiment, the piston rod 112 is connected to the piston (not shown in FIG. 4) which is located within the disposable part 200. Extending from the end of the piston rod 112 that interacts with the piston is a tip 113 with ridges (also referred to as "juice extractor") structured to be received within a complementary-shaped sleeve recess defined in a sleeve 114 disposed in the reusable part 100. The reusable part 100 may include at least a portion of a driving mechanism, for example, a motor and gears (not shown in FIG. 4) which drive the threaded cylindrical sleeve 114. The sleeve 114 is, in some embodiments, configured to receive the piston rod 112, and to transfer rotational movement to the ridged-tip 113 of the piston rod 112, to thus actuate the piston rod 112. This implementation is described, for example, in co-owned/co-pending International Patent Application No. PCT/IL09/000,388, filed Apr. 7, 2009, claiming priority to U.S. Provisional Patent Application No. 61/123,509, filed Apr. 9, 2008, and entitled "Systems, devices and methods for fluid delivery", the content of which is hereby incorporated by reference in its entirety. Additionally, a notifier/indicator, e.g., a buzzer (not shown in FIG. 4), may be positioned in the reusable part 100 of the dispensing unit 10 (see, for example, FIG. 5).

Figure 5:
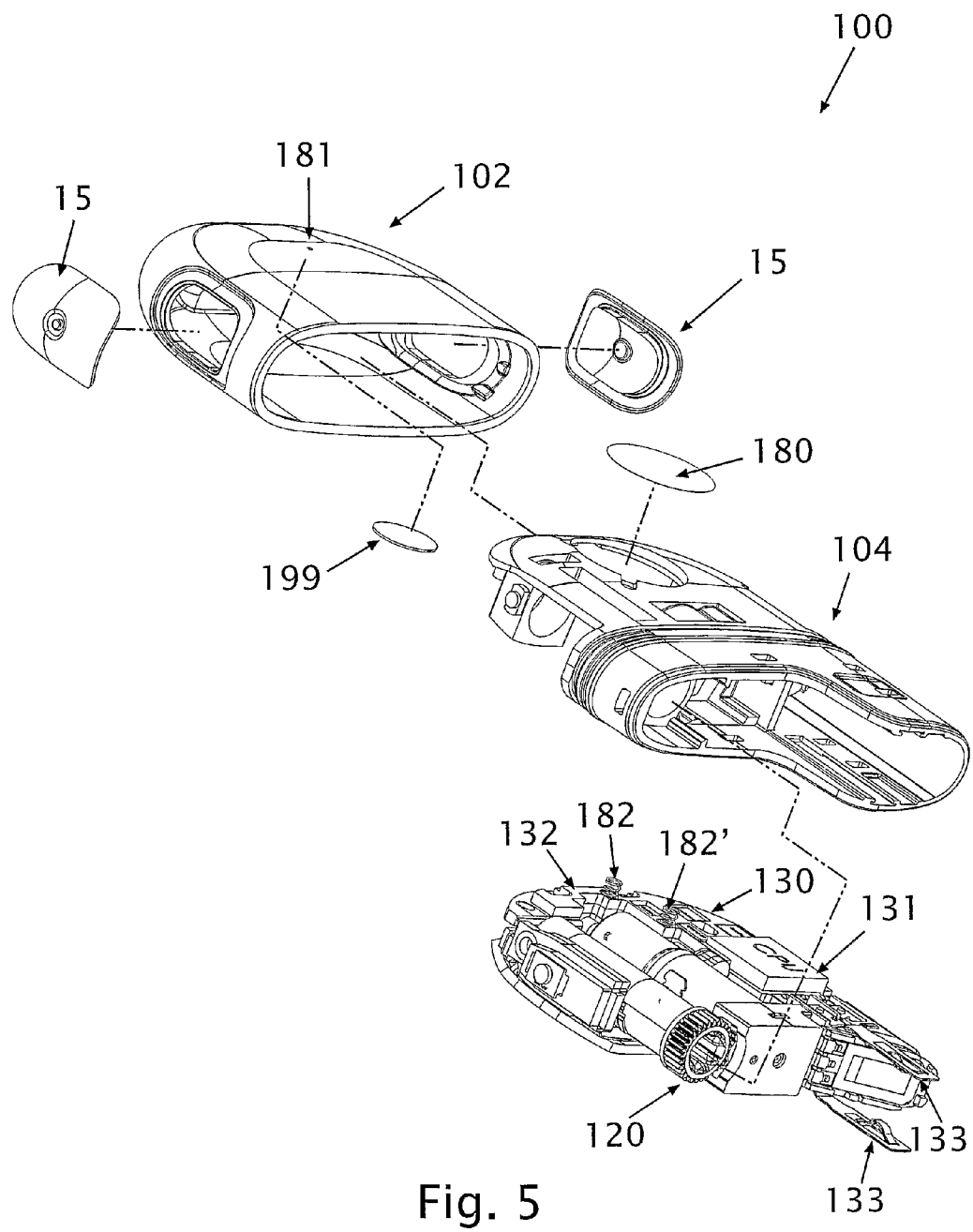
FIG. 5 is a partial exploded view of the reusable part shown in FIG. 4.

Referring to FIG. 5, a partial exploded view of the reusable part 100 of FIG. 4 is shown. In some embodiments, the reusable part 100 comprises an electronic arrangement 130 that includes the various electronically-implemented modules of the dispensing unit 10 (such as a controller 131, e.g., a CPU-based controller, antenna, RF modem), and at least a portion of the driving mechanism 120, which may be positioned within a reusable chassis 104. The reusable part 100 may further comprise an auditory notifier (buzzer) 180. In some embodiments, the buzzer 180 is configured as a piezoelectric diaphragm comprising a piezoelectric element, as described in detail in FIGS. 6a-6c. For the purpose of the present disclosure, the terms "piezoelectric buzzer", "piezoelectric diaphragm" and "piezoelectric element" may be used interchangeably to describe a piezoelectric-type auditory notifier. The buzzer 180 may be connected to the controller 131, e.g., CPU (or some other electronic module) via electrical contacts, e.g., two springs 182, 182', which may be soldered or similarly secured to a Printed Circuit Board ("PCB") 132. In some embodiments the buzzer 180 may be coupled/secured to a reusable chassis 104 and/or to a reusable housing 102 in various ways such as by adherence (e.g., via glue), ultrasonic soldering, laser welding or the like. In other embodiments, the buzzer 180 is merely supported by the springs 182, 182', which may hold/press the buzzer 180 against the reusable chassis 104 and/or the reusable housing 102. Proper positioning and securing of the buzzer 180 is necessary to produce adequate sound pressure levels.

In some embodiments, the reusable housing 102 includes an aperture/hole 181 to allow air flow between the internal cavity of the dispensing unit 10 and the external environment. The aperture 181 (also referred to as "sound emitting aperture") is, in some embodiments, positioned in the vicinity of the buzzer 180 to facilitate transmission of the sound/vibrations produced by the buzzer 180 to the outside of the dispensing unit 10, thus improving the efficiency of the alarm function of the dispensing unit 10. In some embodiments, the position of the aperture 181 in the reusable housing 102 is such that upon insertion of the reusable chassis 104 into, at least partly, the reusable housing 102, the aperture 181 is located directly above (or below) the buzzer 180. According to some embodiments, the aperture 181 is aligned with the center of the buzzer 180, to increase the efficiency of the alarm capabilities of the dispensing device. In some embodiments the aperture/hole 181 is provided in the housing of the disposable part 200 of the dispensing unit 10. In some embodiments both the reusable housing 102 and the housing of the disposable part 200 include such apertures. In some embodiments, the aperture 181 is also required to allow ambient air penetration required for power supply such as a Zinc-air battery, as described, for example, in co-pending/co-owned International Patent publication no. WO/2009/013734, filed Jul. 20, 2008, claiming priority to U.S. Provisional Application No. 60/961,484, filed Jul. 20, 2007, the contents of which are hereby incorporated by reference in their entireties.

In some embodiments, in order to ensure that the dispensing unit 10 is sealed and waterproof, the aperture 181 is provided with a selective membrane (e.g., a Gore-Tex ® membrane) 199, which enables air/gas passage and prevents liquid ingression. A sealable aperture of a dispensing unit is disclosed in co-pending/co-owned International Patent publication no. WO/2009/013735, filed Jul. 20, 2008, claiming priority to U.S. Provisional Application Ser. No. 60/961,382, filed Jul. 20, 2007, the contents of which are hereby incorporated by reference in their entireties. In some embodiments, the sealing of the dispensing unit 10 is also achieved by employing, for example, at least one gasket (not shown in FIG. 5) coupled to the housing of the reusable part 100 and/or to the housing of the disposable part 200. The gasket(s) can also be coupled to the chassis of the reusable part 100 and/or to the chassis of the disposable part 200.

Figure 6A:
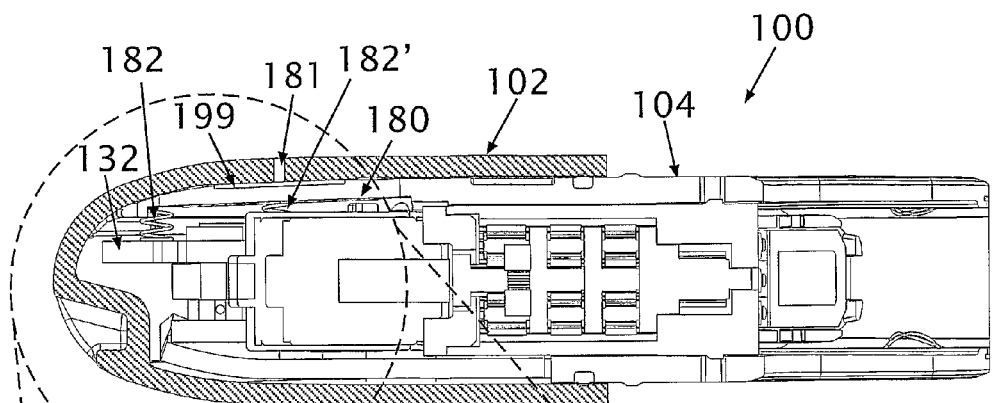
FIGS. 6a-6c are cross-sectional views of the reusable part of FIG. 4 employing a buzzer according to some embodiments of the disclosure.
Figure 6B:
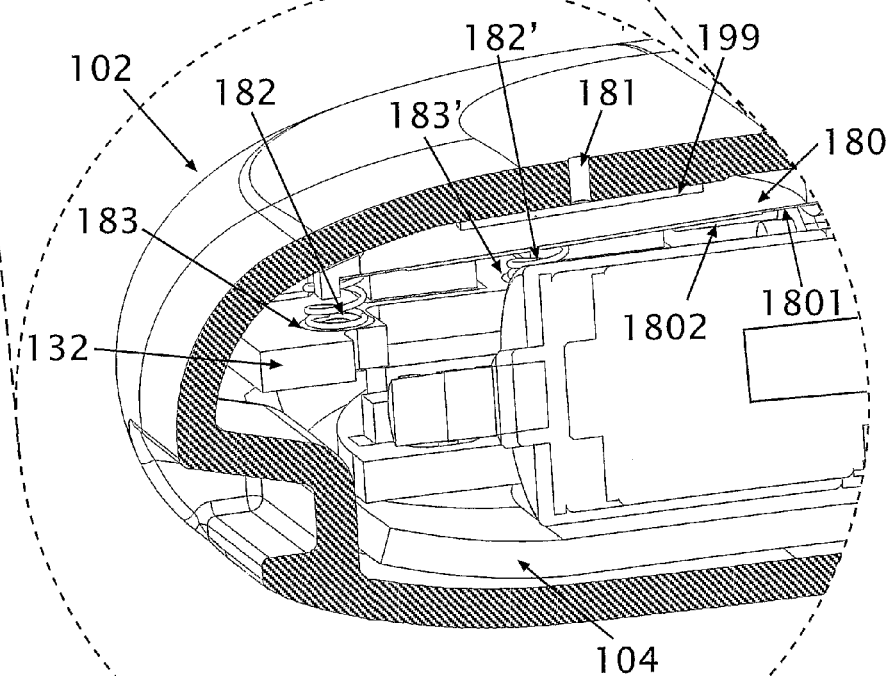
Figure 6C:
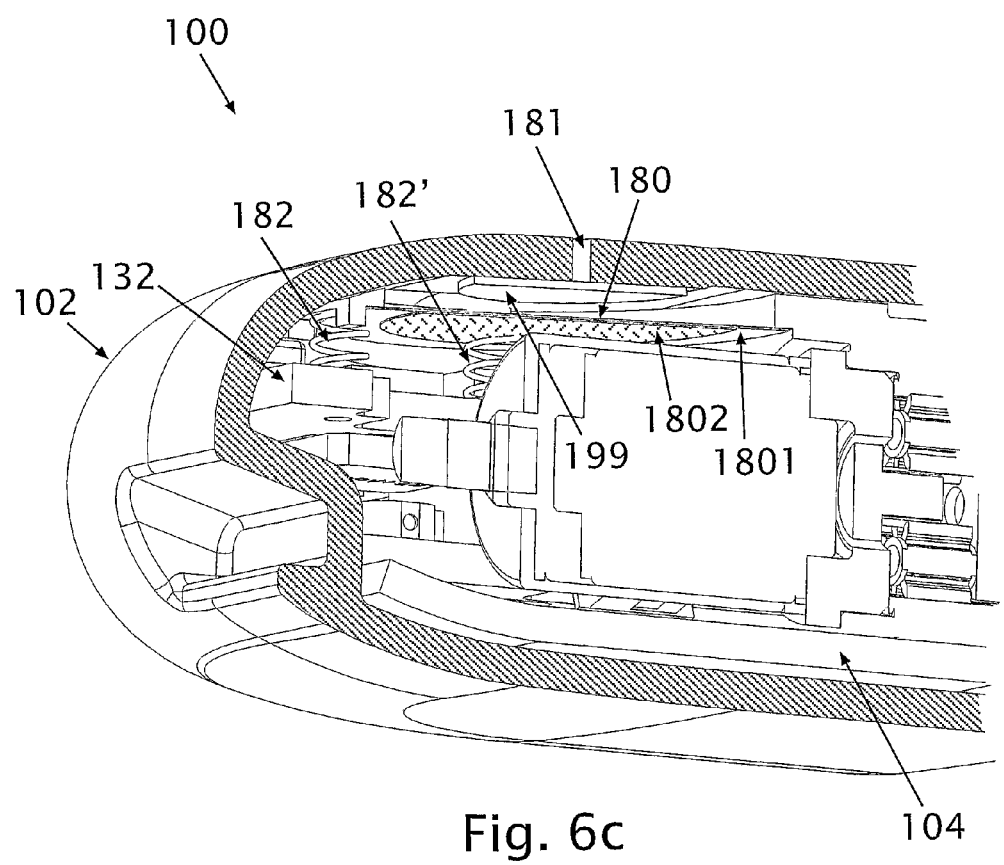

Referring to FIGS. 6a-6c, cross-sectional views of the reusable part 100 of FIG. 4 employing a buzzer 180 are shown. The buzzer 180 may be configured as a piezoelectric diaphragm, and may include a piezoelectric plate (e.g., a ceramic plate, crystal plate) 1802 having electrodes on both sides (e.g., silver electrodes), and a metal plate 1801 (e.g., a brass plate, a stainless-steel plate), which is larger than the piezoelectric plate 1802. The piezoelectric plate 1802 and the metal plate 1801 may be round, square, or any other shape. For the purpose of this disclosure the terms "plate" and "disc" may be used interchangeably without limiting the shape of the plates to a rounded shape. The piezoelectric plate 1802 may be attached to the metal plate 1801 using an adhesive. According to some embodiments, the buzzer 180 may be coupled/secured to the reusable chassis 104 by gluing, ultrasonic soldering, laser welding and the like. The buzzer 180 may be coupled to the chassis 104 at the edge of the metal plate 1801, such that the whole plate 1801 may vibrate up and down, thus increasing the effectiveness of the buzzer 180. Two springs 182, 182' may be soldered (or similarly connected) to the PCB 132 over conductive pads 183, 183' respectively, and may be positioned such that one spring 182 is in contact with the metal disc 1801, and the other spring 182' is in contact with the piezoelectric disc 1802 (or, more specifically, with its outwardly facing electrode), as shown in FIG. 6c. The buzzer 180 may be controlled (including activating the buzzer) by a controller, such as a controller implemented, for example, using a CPU (not shown in FIGS. 6a-6c) by causing voltage to be applied to the buzzer 180 via the two springs 182, 182'. In some embodiments, the buzzer 180 is driven by applying alternating voltage or periodic voltage (i.e., the voltage reverses direction in regular cycles). Applying alternating/periodic voltage between the electrodes of the buzzer 180 causes flexing of the buzzer 180 due to the piezoelectric effect (i.e., shrinking and expanding of piezoelectric material as a result from applying electrical voltage), and as a result sound/acoustic waves are generated. In the embodiment shown in FIGS. 6a-6c, a portion of the reusable housing 102 is configured to function as a one-sided resonance chamber for the buzzer 180. In general, a resonance chamber is typically configured as a cavity defined by interior surfaces that reflect acoustic/sound waves. A two-sided resonance chamber includes two interior surfaces positioned on opposite sides of the buzzer 180 (substantially parallel to the buzzer) for reflecting acoustic waves generated by the buzzer 180 in both directions, whereas a one-sided resonance chamber generally comprises one such internal surface, positioned on only one side of the buzzer 180. Therefore, when the buzzer is placed in a one-sided resonance chamber only the acoustic waves which are generated in the direction of the reflecting surface bounce back and forth between the buzzer and the surface. Accordingly, in some embodiments, the buzzer 180 is positioned within the reusable part housing 102 such that a portion of an interior surface of the housing 102, in some embodiments the interior surface which includes the aperture 181, reflects the acoustic/sound waves generated by the buzzer 180 and the acoustic/sound waves may bounce back and forth from the buzzer 180 to that interior surface of the housing 102 with minimal loss, thus amplifying the sound level produced by the buzzer 180. A portion of the reusable chassis 104 may constitute side (or circumferential) walls of the resonance chamber. In some embodiments, the properties of the resonance chamber may be determined according to the expected/estimated (or nominal) resonant frequency of the buzzer 180 (e.g., the frequency specified by the manufacturer or a frequency found via experiments). Such properties may include material, wall thickness, chamber dimensions (i.e., depth), etc.

Figure 7:
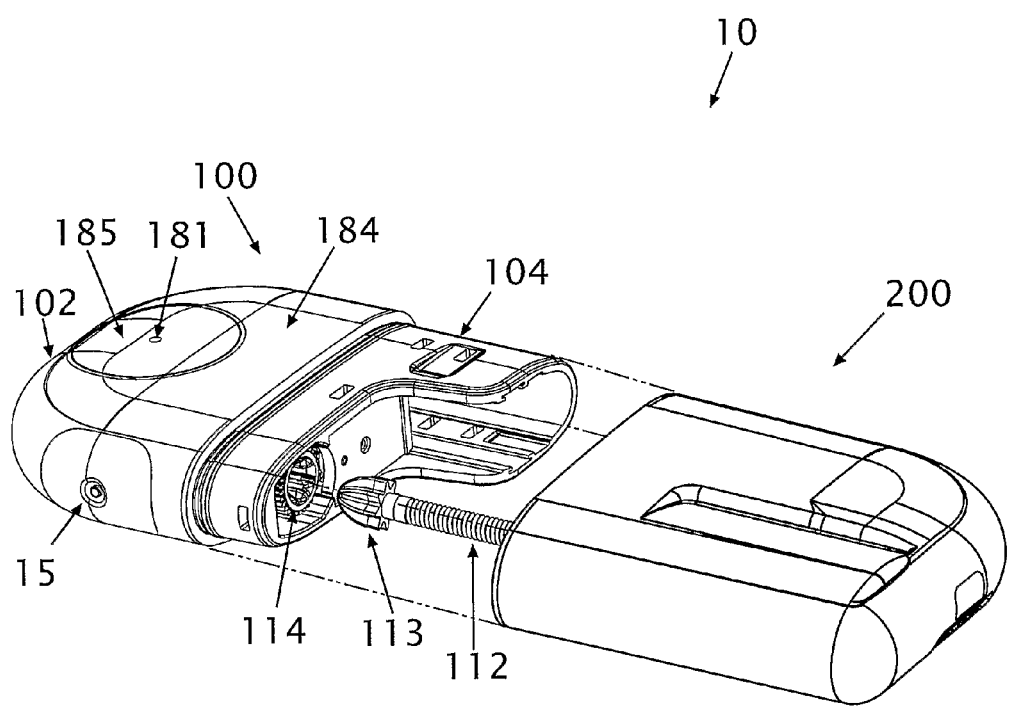
FIG. 7 is a perspective view of a dispensing unit that includes an auditory notifier (e.g., buzzer) according to some embodiments of the disclosure.

Referring to FIG. 7, a perspective view of another dispensing unit that includes a buzzer is shown. The pumping mechanism and its components may be similar to those described with reference to FIG. 4. In the depicted implementation of FIG. 7, portions of the reusable part housing 102 and the reusable part chassis 104 (which is received, at least partly, within the housing) define a double-sided (or two-sided) resonance chamber for the buzzer 180 (further details are provided below in relation to FIGS. 9a-9b). In some embodiments, the reusable part housing 102 comprises a main portion 184 and a cover portion 185 ("cover"), which may be a separate connectable portion that serves to define interior surfaces of the buzzer's resonance chamber. The cover 185 may be round, oval, rectangular, or any other shape. In some embodiments, the cover 185 comprises a sound emitting aperture/hole 181.

Figure 8:
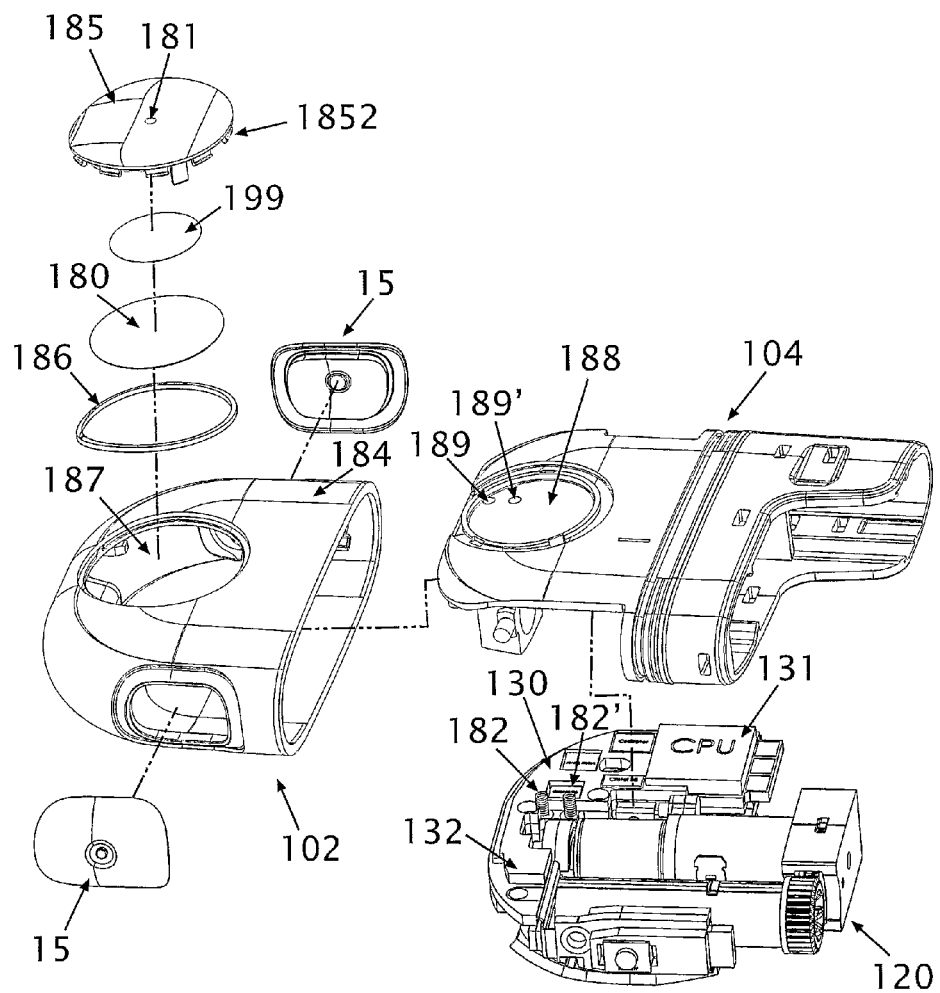
FIG. 8 is a partial exploded view of the reusable part of FIG. 7.

FIG. 8 shows a partial exploded view of the reusable part 100 of FIG. 7. In such embodiments, the reusable part 100 may comprise electronic modules 130 (including, for example, CPU 131, antenna, RF modem) and at least a portion of the driving mechanism 120, which may be positioned within the reusable part chassis 104. In the shown embodiment, the reusable part chassis 104 comprises a buzzer chamber portion 188, i.e., a portion which serves as one of the interior surfaces of the buzzer's 180 resonance chamber. The buzzer chamber portion 188 (the "chamber portion") can be round, oval, rectangular, or any other shape. The chamber portion 188 may include two conduits 189, 189' to receive the two springs 182, 182' used for transferring voltage to the buzzer 180. The main portion 184 of the reusable housing 102 may include an opening 187 which, in some embodiments, has the size and shape of the cover portion 185 so that it can be hermetically closed by the cover portion 185.

The cover 185 may include an aperture 181 provided with a selective membrane (e.g., a Gore-Tex® membrane) 199 which is attached to the cover 185, as described, for example, with reference to FIG. 5. In some embodiments, the position of the aperture 181 in the cover 185 is such that upon assembly of the reusable part 100, the aperture 181 is located directly above (or below) the buzzer 180. According to some embodiments, the aperture 181 is aligned with the center of the buzzer 180, to increase the efficiency of the alarm capabilities of the dispensing device. The cover 185 may further include at least one latch 1852, or any other securing mechanism, to enable secure connection of the cover portion 185 to the main portion 184. A gasket 186, or any other sealing mechanism, may be provided for sealing the reusable part housing 102 upon connection of the cover portion 185 to the main portion 184. In some embodiments, the buzzer 180 may be coupled to the cover 185 by gluing, ultrasonic soldering, laser welding and the like. In some embodiments, the buzzer 180 may be coupled to the chassis 104. In some embodiments the buzzer 180 is coupled to neither the cover 185 nor to the chassis 104, and the secure positioning of the buzzer 180 is instead achieved by the attachment of the cover portion 185 to the reusable chassis 104 with the buzzer 180 positioned therebetween. According to some embodiments, upon attachment of the cover 185 to the chassis 104 the buzzer 180 is supported by the cover 185 and the chassis 104, at the edge of the metal plate 1801, as shown in FIGS. 9a-9b, so that the whole plate 1801 may vibrate up and down upon voltage application, thus increasing the effectiveness of the buzzer 180.

Figure 9B:
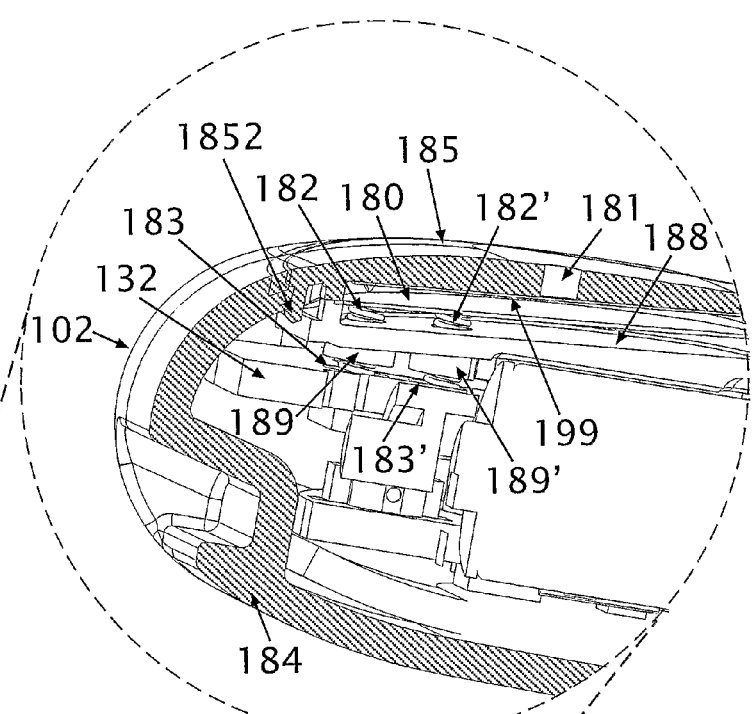
FIGS. 9a-9b are cross-sectional views of the reusable part of FIG. 7.
Figure 9A:
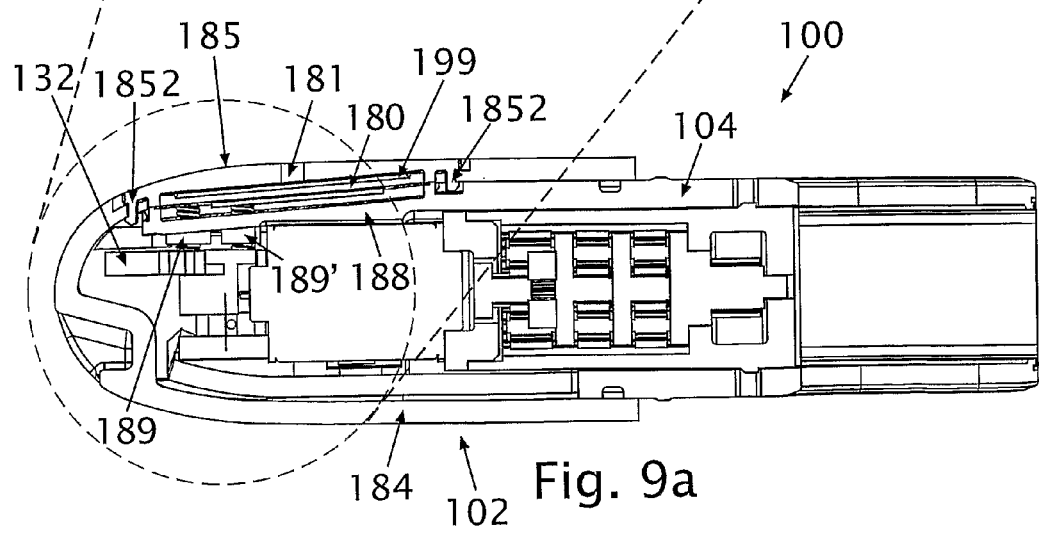

FIGS. 9a-9b illustrate cross-sectional views of the reusable part of FIG. 7. The cover 185 is connected to the main portion 184 of the reusable housing 102 using one or more anchoring mechanisms (e.g., latches) 1852. The cover 185 and the chamber portion 188 of the reusable chassis 104 constitute together a double-sided resonance chamber for the buzzer 180. The buzzer 180 may be coupled to the cover 185 or to the chassis 104. As noted, the chamber portion 188 may be provided with two conduits (or bores) 189, 189', through which the two springs 182, 182', which serve as electrical contacts for the buzzer 180, pass. The springs 182 and 182' may be coupled to conductive pads 183, 183' located on the PCB 132. The springs 182, 182' can be soldered (or similarly attached) to the PCB 132. In circumstances in which the springs 182, 182' are not soldered to the PCB 132, the conduits 189, 189' may also provide proper alignment of the springs 182, 182' relative to the buzzer 180 and the conductive pads 183, 183' on the PCB 132. The activation of the buzzer 180 may be performed in a manner similar to that described in relation to FIGS. 6a-6c.

The sound generated by the buzzer can be further amplified by activating it at or near its resonant frequency. However, the resonant frequency of a piezoelectric element typically has a significant tolerance (e.g. ±15%), and it may also be affected by its assembly within the dispensing unit, for example, by the method of securing (coupling) the buzzer to the housing/chassis of the unit, including the contact points/areas between the buzzer and the housing/chassis. For example, the buzzer may be mounted at the node, i.e., at the location of the outer circumference of the piezoelectric plate, where no vibration takes place, or at its edges (thus, effectively, moving the node). In some embodiments, the buzzer resonant frequency may also be affected by the connection of a new disposable part to the reusable part, which may effectively alter the properties of the resonance chamber (e.g., dimensional properties) due to disposable part manufacturing and/or assembly tolerances, for example. In light of the above, driving the buzzer at its nominal/expected frequency (e.g., the frequency specified by the manufacturer or a frequency found beforehand via experiments) may result in lower sound pressure levels than desired. Therefore, in some embodiments, the controller of the dispensing unit may be configured to perform a calibration (e.g., self-calibration) procedure to determine the actual resonant frequency of the buzzer and then determine, based on the determined actual buzzer resonant frequency, the frequency (or frequencies) for activating/driving the buzzer to achieve maximal/optimal audible output. FIGS. 10-14b illustrate examples of such calibration procedures. Buzzer calibration (including self-calibration) procedures described herein may be performed using two electrical contacts (e.g., the two springs 182, 182' depicted in FIGS. 5-9b).

Figure 10:
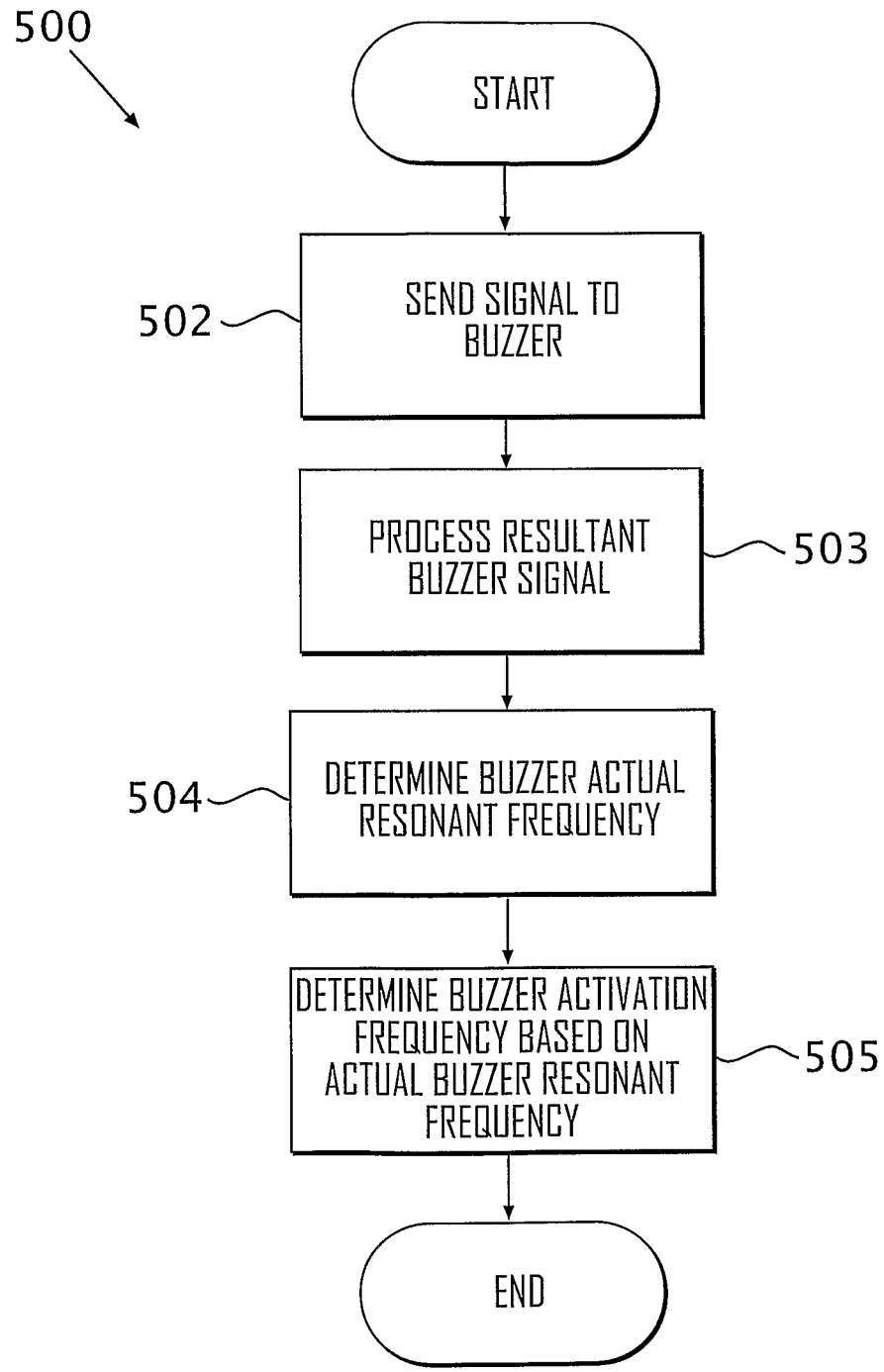
FIG. 10 is a flow diagram of a buzzer self-calibration procedure according to some embodiments of the disclosure.

Referring to FIG. 10, a flow diagram of a buzzer calibration procedure 500 is shown. Initially, a signal (as described herein, the term "signal" may refer to a single pulse or to a series of pulses), which may have pre-determined characteristics (e.g., pre-determined duration, pre-determined amplitude, pre-determined frequency, etc., with such pre-determined characteristics being selected, for example, by the manufacturer and/or by a user or an operator, such as a technician, prior to performing a calibration procedure), is sent 502 to the buzzer by a controller (e.g., CPU). The driving signals (used for the calibration operation) may include sinusoidal waves, square waves, etc. In other words, voltage is applied to the buzzer via the two electrical contacts (e.g., the two springs 182, 182'). In some embodiments, alternating (or periodic) voltage may be applied to the buzzer. Removal of the excitation, i.e., disconnection of the electrical contacts from the power supply, causes the buzzer to vibrate, at its actual resonant frequency (the resonant frequency of a system that includes a notifier will depend on characteristics of the notifier and characteristics of the environment in which the notifier operates), thus generating an acoustic signal. The resultant generated buzzer signal is subsequently processed 503 by the controller (e.g., CPU). In some embodiments a separate component, e.g., an analog-to-digital converter (or ADC), may be used to sample the resultant buzzer signal prior to processing. The actual resonant frequency of the buzzer is then determined 504 according to one or more properties/characteristics of the resultant generated buzzer signal, including such properties as the amplitude (voltage level), signal period and other characteristics of the generated buzzer signal.

Figure 12:
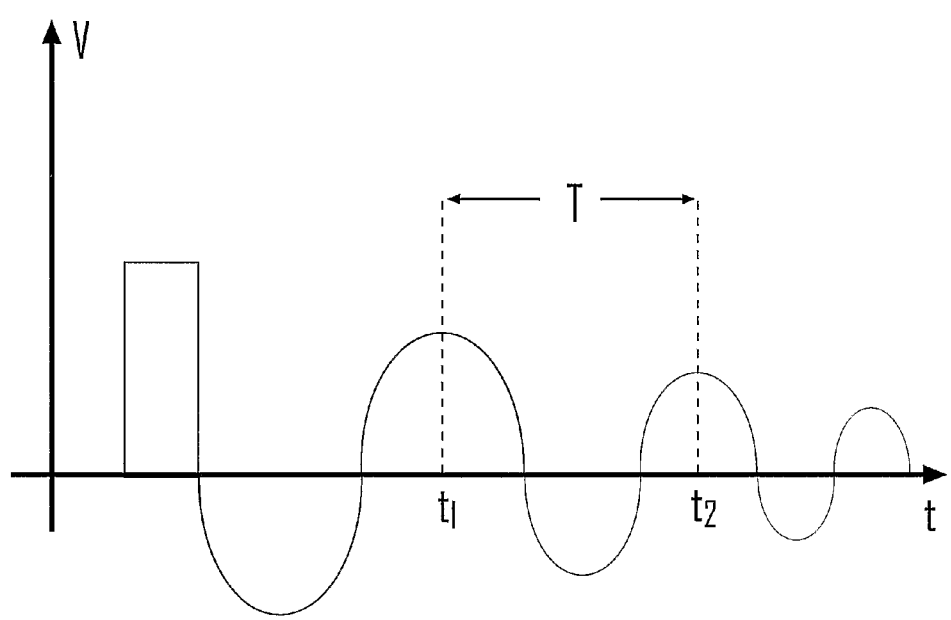
FIG. 12 is a graph illustrating the oscillation behavior of a buzzer signal generated in response to the transmission of an activation signal according to some embodiments of the disclosure.

As explained in greater details with respect, to FIG. 12, determining the actual resonant frequency of a system that includes a notifier may be performed by measuring the period of the acoustic signal (i.e., the time interval between successive oscillatory cycles). In some implementations, commercial frequency analyzers or other types of instruments configured to determine signal behavior may be used to determine the actual resonant frequency. In some embodiments, the properties/characteristics of the driving pulse/signal which was sent to the buzzer by the controller (e.g., its frequency) can also be significant when determining the buzzer's actual resonant frequency. For example, in some embodiments, which are described in more detail below in relation to FIGS. 13-14b, a frequency sweep is performed, and the frequency with respect to which the amplitude of the generated buzzer signal is the greatest and/or the duration of residual oscillations is the longest, may be deemed to be the buzzer's actual resonant frequency. One or more activation/driving frequencies for the buzzer (i.e., the frequencies of the activation/driving signal for generating notifications) are then determined 505 based on the actual resonant frequency of the buzzer (e.g., the resonant frequency of the buzzer when operating in its current environment, including the buzzer's position within the housing in which the buzzer is retained, and the housing's shape and configuration). In some embodiments the actual resonant frequency of the buzzer is set as a buzzer driving frequency, whereas in other embodiments the buzzer's actual resonant frequency is only one factor taken into account when determining the optimal frequency of the buzzer driving signal. In some embodiments, upon determining the buzzer's actual resonant frequency, the buzzer may be activated in several different frequencies slightly higher or lower than its actual resonant frequency, such that each activation frequency, or a specific sequence of activation frequencies, correlates to one or more specific functions/notifications/messages. Under those circumstances, the controller of the dispensing device may thus be configured to select a signal sequence from a plurality of signal sequences, with each of the plurality of signal sequences including one or more signals (i.e., a signal sequence may comprise just a single signal that is applied to the notifier) having respective pre-determined characteristics (e.g., frequency, duration, amplitude), with each of those signal sequences, when applied to the buzzer, causing corresponding one or more auditory/acoustic signals (or acoustic signal sequences) to be generated. Each of those generated signals (or signal sequences) may be representative of one or more different operating conditions of the therapeutic fluid dispensing device, including such conditions corresponding to alarm conditions, status notifications and/or required action alerts (e.g., commencement of bolus delivery, low battery, occlusion, mechanical malfunction, etc.). The controller then applies the selected signal sequence to the buzzer. The activation signals (or signal sequences) and/or the resultant acoustic signals (or signal sequences) may include sinusoidal waves, square waves, etc.

In some embodiments, in the course of performing a calibration procedure, the calibration procedure may be performed without the user being distracted, or otherwise being interrupted, by the acoustic signals being generated. For example, in some embodiments, the amplitude of the acoustic signal is maintained below an audible threshold so that it would have a low volume that the user cannot hear. Thus, in some embodiments, the controller configured to, for example, perform the calibration procedure may apply one or more calibration signals (or cause one or more signals to be applied) to calibrate the notifier within the device (e.g., determine the resonant frequency). Each of the one or more applied signals may have at least one pre-determined characteristic (e.g., pre-determined amplitude, duration, frequency, etc.) resulting in the generation of respective one or more acoustic signals that each may have an amplitude lower than a pre-determined audible threshold representative of a minimum amplitude level detectable by a user.

Figure 11:
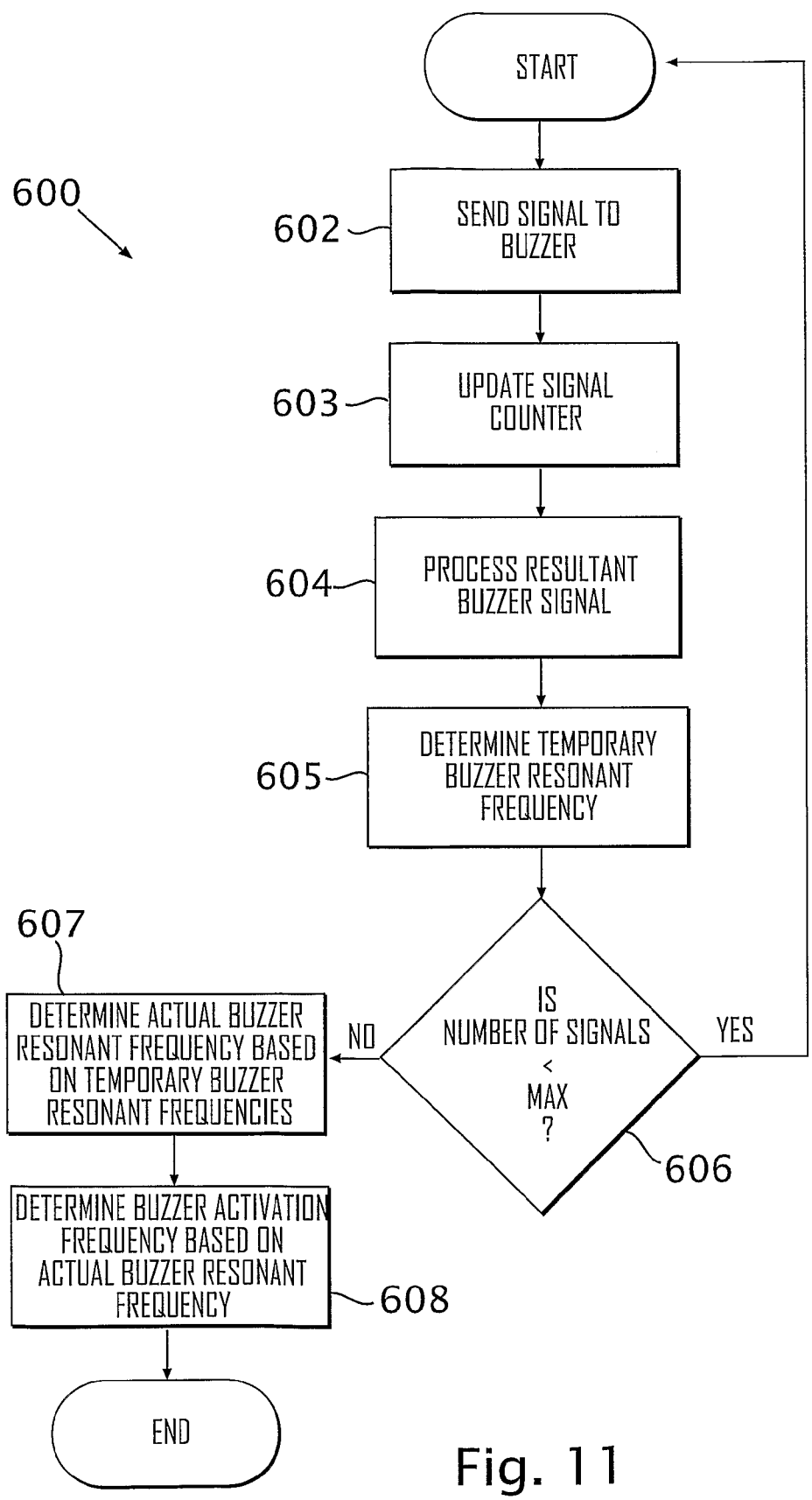
FIG. 11 is a flow diagram of another buzzer self-calibration procedure according to some embodiments of the disclosure.

Referring to FIG. 11, a flow diagram of a buzzer calibration procedure 600 is shown. Initially, a calibration signal (e.g., a single pulse or a series of pulses) may be sent 602 to the buzzer by the controller (e.g., CPU). In other words, voltage is applied between the electrodes of the piezoelectric element. A signal counter may then be updated 603 (signals sent simultaneously to the two buzzer discs to achieve a potential difference between the electrodes may be considered a single signal). The counting may be performed by the controller or by a separate counter. As a result of the application of the signal, the buzzer vibrates at its actual resonant frequency (i.e., once the application of the excitation/activation signal is suspended). The resultant generated buzzer oscillation signal is then processed (and/or analyzed) 604 by the controller in order to determine its frequency (i.e., the buzzer's actual resonant frequency). The processing/analyzing may include finding the period of a resultant substantially sinusoidal wave, as further described in relation to FIG. 12. In some embodiments a separate component, e.g. ADC, may be used to sample the resultant buzzer signal prior to processing. In some embodiments the actual resonant frequency of the buzzer is determined after application of a single signal to the buzzer. In some embodiments, the process may be repeated several times (e.g., an iterative process). Accordingly, in some embodiments, after each signal application, a temporary buzzer resonant frequency may be subsequently determined 605, based on the corresponding resultant buzzer signal, and stored in a memory of the dispensing unit. The signal counter may then be checked 606 to determine if the number of sent signals is lower than a pre-determined maximum value. If the number of sent signals is lower than the pre-determined maximum signal number, then the operations 602-605 may be repeated. If not (i.e., if the number of signals sent matches the pre-determined maximum signal number), then the actual resonant frequency of the buzzer may be determined 607 based on the temporary (intermediate) resonant frequencies which were determined in step 605. In some embodiments, the buzzer resonant frequency may be determined as the average of the temporary resonant frequencies. The frequency of the activation/driving signal for the buzzer (i.e., in order to generate notifications) is then determined 608 based, at least in part, on the actual resonant frequency of the buzzer. In some embodiments the actual resonant frequency of the buzzer is set as the frequency of the buzzer activation/driving signal, whereas in other embodiments the buzzer's actual resonant frequency is only one factor taken into account when determining the optimal frequency of the buzzer activation/driving signal. As stated above, in some embodiments, after the calibration procedure has been completed, the buzzer may be activated (i.e., to generate notifications/alerts) in several different frequencies slightly higher/lower than its actual resonant frequency, such that each activation frequency, or a specific sequence of activation frequencies, correlates to one or more specific functions/notifications/messages. Thus, the calibration process may yield several activation signals, or sequences of activation signals, to produce different sounds, with each sound (or sound sequence) corresponding to one or more different operating conditions of the medical device that includes the notifier (e.g., a notification of a particular device status, an alarm sound to alert the occurrence of a particular event, etc.).

As stated above, in some embodiments, a signal is sent to the buzzer only once and the actual resonant frequency of the buzzer is determined based on the properties/characteristics of the single resultant buzzer oscillation signal. In some embodiments, the properties include, for example, the period of the substantially sinusoidal wave, as shown in FIG. 12.

Referring to FIG. 12, a graph illustrating the behavior of an acoustic (auditory) signal, generated in response to the transmission of an activation signal (e.g., calibration signal), is shown. Based on the behavior resulting from application of the signal, the buzzer's temporary (or final) resonant frequency can be determined (as depicted, for example, in operation 605 shown in FIG. 11). Specifically, after the controller (or CPU) sends a signal (or causes a signal to be sent) to the buzzer, the buzzer oscillates at its actual resonant frequency (i.e., the frequency at which a piezoelectric element oscillates following excitation of the element within the element's environment, and the suspension of such excitation of the piezoelectric element). The oscillation signal fades over time due, for example, to friction. FIG. 12 shows a graph of the buzzer voltage levels versus time from the time a signal (in the shown example, a single pulse) is sent to the buzzer. Because the buzzer oscillates at its actual resonant frequency, the resonant frequency can be derived from the sinusoidal signal's period (e.g., the time between two consecutive peaks of the signal) according to the following formula:

$$f = \frac{1}{T}.$$

In some embodiments, the controller of the dispensing device may be configured to perform a self-calibration procedure by applying a plurality of signals to the buzzer to generate a corresponding plurality of auditory signals. Since driving the buzzer at (or near) its actual resonant frequency results in stronger buzzer vibrations, the actual resonant frequency can be determined by identifying from the generated plurality of buzzer signals a signal having the largest amplitude of the respective amplitudes of the plurality of generated signals, and then identifying the frequency with respect to which the signal with the largest amplitude was generated. Buzzer activation signal/s is/are then set based on that frequency. The applied driving signals may include sinusoidal waves, square waves, etc.

Figure 13:
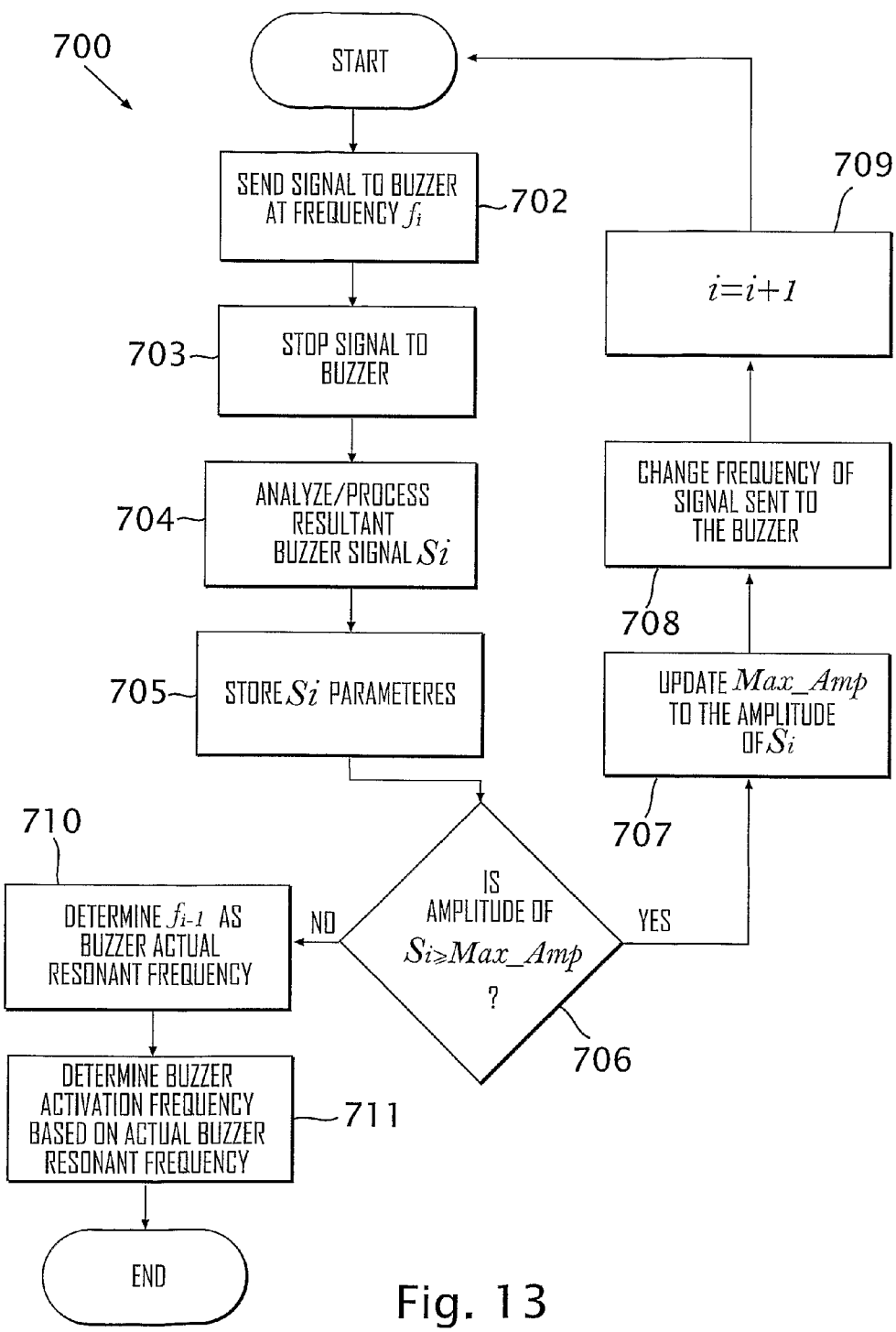
FIG. 13 is a flow diagram of another buzzer self-calibration procedure according to some embodiments of the disclosure.

Referring to FIG. 13, the buzzer is activated at increasing (or decreasing) frequencies through a predetermined frequency range, e.g., between $f_0-\Delta f$ and $f_0+\Delta f$, where $f_0$ is the expected (or nominal) buzzer resonant frequency (e.g., the frequency specified by the manufacturer or a frequency found via preliminary experiments). In other words, an alternating (or periodic) voltage is applied to the buzzer in intervals corresponding to, or close to, the nominal buzzer resonant frequency and to a surrounding frequency range. When the excitation is removed, the frequency of the generated buzzer signal is generally always the same (i.e., its actual resonant frequency). However, driving the buzzer at different frequencies, i.e., by changing the time intervals between consecutive voltage applications, generally causes the buzzer's resonant frequency to have different amplitude responses. For example, an excitation signal having a frequency that is closer to the system's actual frequency will result in an auditory response having a larger initial amplitude than the resulting auditory response generated when the buzzer is driven by a signal with a different frequency. It is to be noted that when the buzzer is activated to generate notifications (i.e., during the routine operation of the pump, rather than, for example, for calibration purposes), the buzzer can be controlled (e.g., excited) to produce particular audio signals having particular frequencies. This is achieved by driving the buzzer at different frequencies, i.e., without letting the buzzer vibrate freely, and instead causing it to vibrate at certain frequencies.

According to the embodiment of FIG. 13, the activation frequency which produces the maximal amplitude from the buzzer is determined as the actual buzzer resonant frequency. Thus, a signal of frequency $f_i$ is sent 702 to the buzzer by the controller (e.g., CPU). The frequency $f_i$ is typically not the expected resonant frequency $f_0$. The frequency sweep can start from a frequency that is either higher (e.g., $f_0+\Delta f$) or lower (e.g., $f_0-\Delta f$) than the expected resonant frequency. The signal transmission is subsequently suspended 703, i.e., voltage is applied a pre-determined number of cycles, after which the buzzer's electrical contacts are disconnected from the power supply (source), to allow sampling of the buzzer signal (as stated above, according to this disclosure the piezoelectric element may comprise only two electrodes, i.e., a feedback electrode is not employed). Upon removal of the excitation, the vibrations of the buzzer continue in a damped manner until they cease altogether. The resultant buzzer signal $S_i$ (i.e., the signal representing the free vibration following removal of the excitation) is then sampled and analyzed/processed 704 by the controller (e.g., CPU). The sampling of the resultant buzzer signal may be carried out by the controller or by a separate component, e.g. ADC. The properties of $S_i$, including, for example, amplitude levels (represented, for example, in volt units), are stored 705. The amplitude of $S_i$ is checked 706 against a maximal value (Max_Amp). The initial maximal value is set to be lower than the amplitude expected to be produced by the buzzer when it is activated at frequencies within the predetermined range $f_0\pm\Delta f$. If the amplitude of $S_i$ is equal to or higher than the current Max_Amp, then the Max_Amp is updated 707 and is set to the amplitude of $S_i$. The frequency of the signal sent to the buzzer is changed 708 (raised/lowered within the predetermined range), and the iteration counter is updated 709. The operations at 702-706 are then repeated.

If, on the other hand, the amplitude of $S_i$ is found, at 706, to be lower than the current Max_Amp, then frequency $f_{i-1}$ (i.e., the frequency that resulted in generation of the current Max_Amp) is determined 710 as the buzzer actual resonant frequency. The frequency of the activation/driving signal for the buzzer (i.e., in order to generate notifications) is then determined 711 based on the actual resonant frequency of the buzzer. In some embodiments the actual resonant frequency of the buzzer is set as the frequency of the buzzer driving signal, whereas in other embodiments the buzzer's actual resonant frequency is only one factor taken into account when determining the optimal frequency of the buzzer driving signal. As stated above, in some embodiments, upon determining the buzzer's actual resonance frequency, several activating signals (or signal sequences) may be set, such that the buzzer may be activated in several different frequencies slightly higher/lower than its actual resonant frequency, with each activation frequency, or a specific sequence of activation frequencies, correlating to one or more specific functions/notifications/messages.

In some embodiments, the frequency sweep continues only until the maximal amplitude is found (the assumption being that there is only one peak corresponding to only one resonant frequency). Alternatively, in some embodiments, the maximal frequency is identified only after the entire frequency range has been swept. According to some embodiments (not shown in FIG. 13), after the properties of $S_i$ are stored, at 705, the value of counter i is compared to a pre-determined value j (for example, i=1 may correspond to frequency $f_0-\Delta f$ and i=j may correspond to frequency $f_0+\Delta f$, or vice versa). If i<j, the frequency of the signal sent to the buzzer is changed (raised/lowered within the predetermined range), the iteration counter is updated (i=i+1), and operations 702-705 are repeated. If i≥j, the amplitudes of all resultant buzzer signals $S_i$(i=1 . . . j) are compared, the frequency that resulted in generation of the signal with the maximal amplitude is determined as the buzzer actual resonant frequency, and the frequency/frequencies of the activation/driving signal/s for the buzzer (i.e., to generate notifications) is/are then determined based on the determined actual resonant frequency of the buzzer.

Figure 14A:
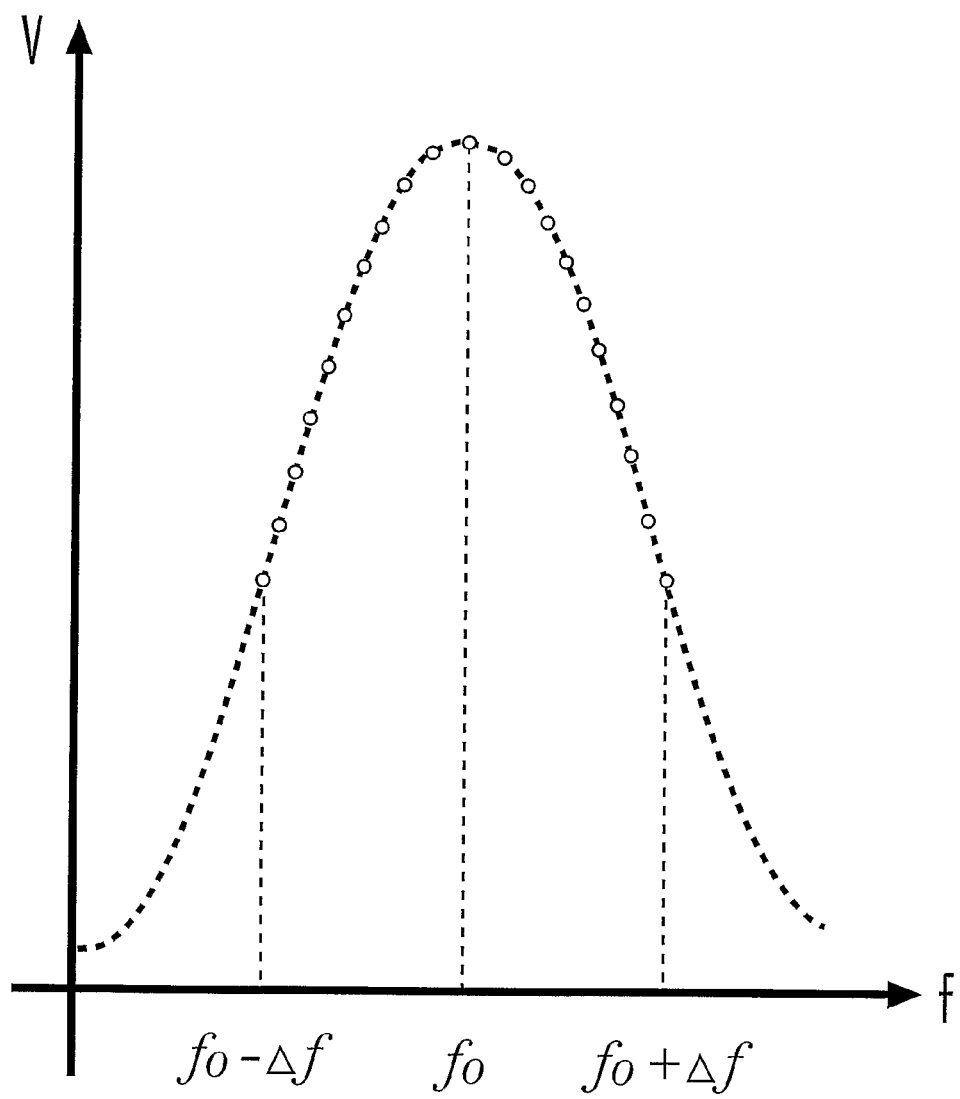
FIGS. 14a-14b are graphs of the amplitude of a signal produced by the buzzer when it is activated at different frequencies according to some embodiments of the disclosure.
Figure 14B:
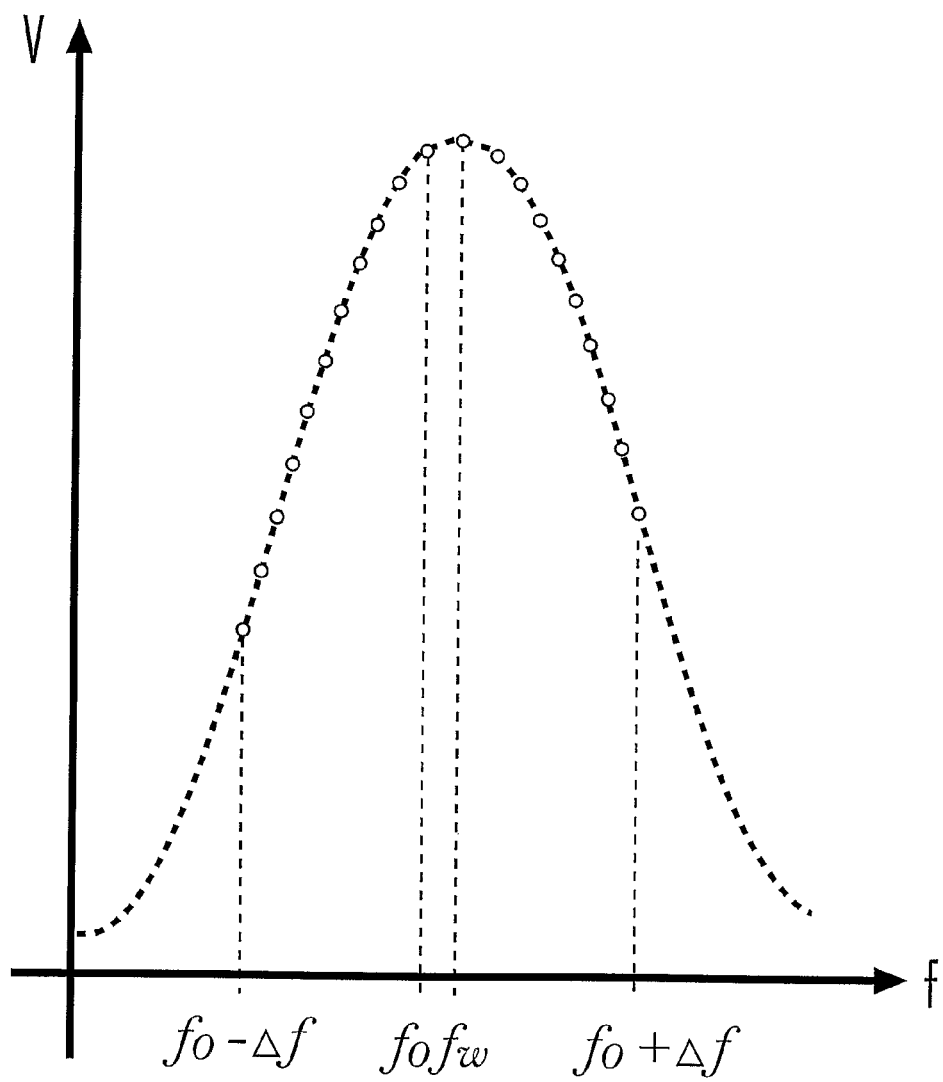

FIGS. 14a-14b illustrate graphs of the amplitude produced by the buzzer when it is activated at different frequencies according, for example, to the procedure 700 described in relation to FIG. 13. As noted, the buzzer is activated at increasing (or decreasing) frequencies through a predetermined frequency range, e.g., between $f_0-\Delta f$ and $f_0+\Delta f$, where $f_0$ is the nominal buzzer resonant frequency (e.g., the frequency specified by the manufacturer or the frequency found via preliminary experiments). As noted, in some embodiments the frequency sweep is discontinued once the maximal amplitude is found, i.e., once the peak of the amplitude graph is reached. In some embodiments, the frequency sweep is continued until the entire predetermined frequency range has been swept, and the stored amplitude levels are then compared in order to find the maximal amplitude achieved. In the example graph shown in FIG. 14a, the maximal amplitude is achieved when activating the buzzer at its expected (nominal) resonant frequency $f_0$. In the example graph shown in FIG. 14b, the maximal amplitude is achieved when activating the buzzer at a frequency $f_\omega$ which is different from the nominal frequency $f_0$, e.g. $f_\omega$ may be slightly higher than $f_0$.

Another self-calibration procedure may be performed by activating the buzzer at increasing (or decreasing) frequencies through a predetermined frequency range, e.g., between $f_0-\Delta f$ and $f_0+\Delta f$, where $f_0$ is the expected buzzer resonant frequency (e.g., the frequency specified by the manufacturer or the frequency found via experiments), and setting an amplitude threshold slightly lower than the amplitude which is expected to be produced by the buzzer when activated at its resonant frequency. According to some embodiments, the resonant frequency is determined as the average of frequencies which generated amplitude above the predetermined threshold (at least the two activation frequencies in which the amplitude threshold was crossed). The frequency/frequencies of the activation/driving signal/s for the buzzer (i.e., in order to generate notifications) is/are then determined based on the determined actual resonant frequency of the buzzer.

Yet another self-calibration procedure may be performed by activating the buzzer at increasing (or decreasing) frequencies through a predetermined frequency range, e.g., between $f_0-\Delta f$ and $f_0+\Delta f$, where $f_0$ is the expected buzzer resonant frequency, in order to find the frequency with respect to which the duration (or "fading duration") of the resultant buzzer signal is the longest. As stated above, when the buzzer is driven at its resonant frequency, its vibrations are the strongest and its residual oscillations last the longest. In some embodiments, the number of low-to-high and/or high-to-low transitions in amplitude is counted for all the resultant signals, and the frequency of the driving signal corresponding to the maximum number of transitions is determined as the actual resonant frequency of the buzzer. The frequency/frequencies of the activation/driving signal/s for the buzzer (i.e., in order to generate notifications) is/are then determined based on the determined actual resonant frequency of the buzzer.

Other calibration (e.g., self-calibration) procedures and/or procedures to determine the actual resonant frequency may be used.

The buzzer calibration processes can be performed, for example, after assembly of the dispensing unit (for a two-part dispensing unit—after assembly of the reusable part), i.e., as part of the assembly line, and/or during priming of the dispensing unit (for a two-part dispensing unit—upon connection of the reusable and disposable parts) prior to use by a patient. In some embodiments the calibration process may be performed periodically, either at predetermined time intervals (e.g., every 12 hours), or at the user's discretion (e.g., an appropriate command can be issued by the user using the remote control unit or the operating buttons provided on the dispensing unit).

Various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. Some embodiments include specific "modules" which may be implemented as digital electronic circuitry, integrated circuitry, specially designed ASICs (application specific integrated circuits), computer hardware, firmware, software, and/or combinations thereof.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, the logic flows depicted in the accompanying figures and described herein do not require the particular order shown, or sequential order, to achieve desirable results.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

What is claimed is:

1. A therapeutic fluid dispensing device to deliver a therapeutic fluid into a body of a patient, the device comprising:
   a controller to control one or more of fluid delivery operations and notification operations;

at least one auditory notifier to produce one or more acoustic signals in response to application of one or more activation signals by the controller;
a plurality of electrical contacts coupled to the at least one auditory notifier to enable the application of the one or more activation signals to the at least one auditory notifier; and
at least one housing retaining the at least one auditory notifier therein, wherein the at least one housing being structured to resonate at least one of the one or more acoustic signals produced by the at least one auditory notifier in response to application of at least one of the one or more activation signals;
wherein the controller includes instructions operating thereon configured to:
determine at least one resonant frequency of the at least one auditory notifier;
apply a plurality of signals to the at least one auditory notifier to generate a corresponding plurality of acoustic signals, each signal in the plurality of applied signals having a corresponding frequency within a frequency range;
identify from the corresponding generated plurality of acoustic signals an acoustic signal having the longest duration of the respective durations of the generated plurality of acoustic signals; and
identify from the plurality of applied signals the applied signal that caused the generation of the acoustic signal having the longest duration.

2. The device according to claim 1, wherein the at least one auditory notifier comprises a piezoelectric element.

3. The device according to claim 1, further comprising at least one chassis received, at least partly, within the at least one housing.

4. The device according to claim 3, wherein the at least one auditory notifier is disposed within a resonance chamber defined by one or more walls of one or more of: the at least one housing and the at least one chassis.

5. The device according to claim 4, wherein the resonance chamber is a one-sided resonance chamber.

6. The device according to claim 4, wherein the resonance chamber is a two-sided resonance chamber.

7. The device according to claim 3, wherein one or more of the at least one housing includes a main portion and a cover portion connectable to the main portion;
wherein the cover portion defines a first side of a two-sided resonance chamber; and
wherein a portion of the at least one chassis defines a second side of the two-sided resonance chamber.

8. The device according to claim 7, further comprising:
a sealing mechanism to maintain sealing of the one or more of the at least one housing upon connection of the cover portion to the main portion.

9. The device according to claim 1, wherein the at least one housing comprises at least one sound emitting aperture.

10. The device according to claim 9, wherein the at least one sound emitting aperture is provided with a selective membrane to prevent ingression of fluids into the device.

11. The device according to claim 3, wherein the at least one chassis includes one or more bores for passage of one or more of the plurality of the electrical contacts therethrough.

12. The device according to claim 1, wherein at least one of the plurality of the electrical contacts includes a spring.

13. The device according to claim 1, wherein the plurality of the electrical contacts comprises two electrical contacts.

14. The device according to claim 1, wherein the at least one housing comprises:
a reusable part housing including at least part of a reusable part of the device; and
a disposable part housing including at least part of a disposable part of the device;
wherein the disposable part is connectable to the reusable part.

15. The device according to claim 14, wherein the at least one auditory notifier is retained within the reusable part housing.

16. The device according to claim 1, wherein the instructions are further configured to:
determine the at least one resonant frequency based on at least one acoustic signal resulting from applying the plurality of signals to the at least one auditory notifier.

17. The device according to claim 16, wherein the plurality of applied signals have pre-determined characteristics including one or more of:
a pre-determined amplitude, a pre-determined frequency and a pre-determined duration.

18. The device according to claim 16, wherein the at least one resultant acoustic signal is substantially sinusoidal, and wherein the instructions are further configured to determine a period of the at least one substantially sinusoidal acoustic signal.

19. The device according to claim 16, wherein the instructions are further configured to:
determine a corresponding intermediate resonant frequency for each of the at least one acoustic signal resulting from application of each of the one or more signals; and
determine the at least one resonant frequency based on the determined intermediate resonant frequency for each of the at least one resulting acoustic signal.

20. The device according to claim 1, wherein the instructions are further configured to:
identify from the corresponding generated plurality of acoustic signals an acoustic signal having the largest amplitude of the respective amplitudes of the generated plurality of acoustic signals; and
identify from the plurality of applied signals the applied signal that caused the generation of the acoustic signal having the largest amplitude.

21. The device according to claim 1, wherein the instructions are further configured to set one or more activation frequencies for the at least one auditory notifier based on the determined resonant frequency.

22. The device according to claim 1, wherein:
the one or more activation signals comprise a plurality of signal sequences,
each of the plurality of signal sequences comprising one or more signals having respective pre-determined characteristics,
each of the plurality of signal sequences when applied to the at least one auditory notifier causes a corresponding one of a plurality of acoustic signal sequences to be generated,
each of the plurality of acoustic signal sequences comprising one or more acoustic signals and being representative of one or more different operating conditions of the therapeutic fluid dispensing device;
and wherein the controller includes instructions operating thereon configured to:
select a signal sequence from the plurality of signal sequences; and
apply the selected signal sequence to the at least one auditory notifier.

23. The device according to claim 22, wherein the different operating conditions of the therapeutic fluid dispensing device include one or more of: an alarm condition, a status notification and a required operation alert.

* * * * *